US009874508B2

(12) United States Patent
Garcia et al.

(10) Patent No.: US 9,874,508 B2
(45) Date of Patent: Jan. 23, 2018

(54) SPECTROPHOTOMETER BASED ON OPTICAL CAUSTICS

(71) Applicants: Antonio A. Garcia, Pembroke Pines, FL (US); Luis Nunez, Elmhurst, IA (US); Vladimiro Mujica, Pembroke Pines, FL (US)

(72) Inventors: Antonio A. Garcia, Pembroke Pines, FL (US); Luis Nunez, Elmhurst, IA (US); Vladimiro Mujica, Pembroke Pines, FL (US)

(73) Assignee: Iasotek, LLC., Rockville, MD (US)

( * ) Notice: Subject to any disclaimer, the term of this patent is extended or adjusted under 35 U.S.C. 154(b) by 126 days.

(21) Appl. No.: 14/912,852

(22) PCT Filed: Apr. 8, 2014

(86) PCT No.: PCT/US2014/033386
§ 371 (c)(1),
(2) Date: Feb. 18, 2016

(87) PCT Pub. No.: WO2015/026398
PCT Pub. Date: Feb. 26, 2015

(65) Prior Publication Data

US 2017/0268977 A1 Sep. 21, 2017

Related U.S. Application Data

(63) Continuation of application No. 13/987,658, filed on Aug. 19, 2013, now abandoned.

(51) Int. Cl.
*G01N 15/02* (2006.01)
*G01B 11/24* (2006.01)
(Continued)

(52) U.S. Cl.
CPC ... *G01N 15/0205* (2013.01); *G01N 33/54346* (2013.01); *G01N 33/553* (2013.01);
(Continued)

(58) Field of Classification Search
None
See application file for complete search history.

(56) References Cited

U.S. PATENT DOCUMENTS 3,795,813 A * 3/1974 Kunath .................. H01J 29/58 250/396 R
3,879,128 A 4/1975 Presby
(Continued)

OTHER PUBLICATIONS

Conrad, tracking diseases with GIS, Arc User, pp. 1-3 available at: https://hal-brgm.archives-ouvertes.fr/hal-00546916, accessed on Nov. 6, 2014.
(Continued)

*Primary Examiner* — Tri Ton
*Assistant Examiner* — Jarreas C Underwood
(74) *Attorney, Agent, or Firm* — Kramer Amado, P.C.

(57) ABSTRACT

An apparatus for particle size and a distribution of a population of particle measurements, comprising: a non-monochromatic light source that emits a plurality of a non-monochromatic rays, a medium that includes a particle, wherein the medium is a liquid phase and the particle is suspended within the medium to form a particle-suspension, a droplet of the particle-suspension wherein the droplet is provided with a curved surface, and a detector that is provided with a light providing element.

21 Claims, 23 Drawing Sheets

(51) Int. Cl.

| | |
|---|---|
| ***G02B 6/00*** | (2006.01) |
| ***G01M 11/00*** | (2006.01) |
| ***G01N 33/569*** | (2006.01) |
| ***G01N 33/543*** | (2006.01) |
| ***G01N 33/553*** | (2006.01) |
| *G01N 15/00* | (2006.01) |
| *G02B 6/26* | (2006.01) |
| *G01N 21/88* | (2006.01) |

(52) U.S. Cl.

CPC ........ *G01N 33/56983* (2013.01); *G01B 11/24* (2013.01); *G01M 11/37* (2013.01); *G01N 2015/0065* (2013.01); *G01N 2021/8835* (2013.01); *G01N 2333/185* (2013.01); *G02B 6/262* (2013.01)

(56) References Cited

U.S. PATENT DOCUMENTS 3,922,682 A * 11/1975 Hyde ..................... H01Q 19/19 343/761
4,102,661 A 7/1978 Dudderar et al.
4,312,329 A * 1/1982 Carver ....................... F24J 2/13 126/607
5,270,825 A * 12/1993 Takasugi ................ A61B 1/042 348/335
5,416,586 A * 5/1995 Tronolone ........... G01B 11/255 356/513
5,586,013 A * 12/1996 Winston .................. F21V 7/005 362/294
6,639,733 B2 * 10/2003 Minano ..................... F21V 7/04 257/E33.059
7,187,441 B1 3/2007 Sevick-Muraca et al.
9,581,812 B2 * 2/2017 Warren .............. G02B 27/0025
2003/0016539 A1 * 1/2003 Minano ..................... F21V 7/04 362/347
2005/0221361 A1 10/2005 Norman
2009/0308377 A1 * 12/2009 Kleinwaechter ....... A01G 9/243 126/605
2010/0225913 A1 9/2010 Trainer
2011/0246089 A1 10/2011 Barrett et al.
2012/0264113 A1 10/2012 Garcia et al.
2013/0050689 A1 2/2013 Reich et al.

OTHER PUBLICATIONS

Leroy, et al., “Predicting the surface tension of aqueous 1:1 electrolyte solutions at high salinity”, https://hal-brgm.archives-ouvertes.fr/hal-00546916, 2010, 5427-5442.

* cited by examiner

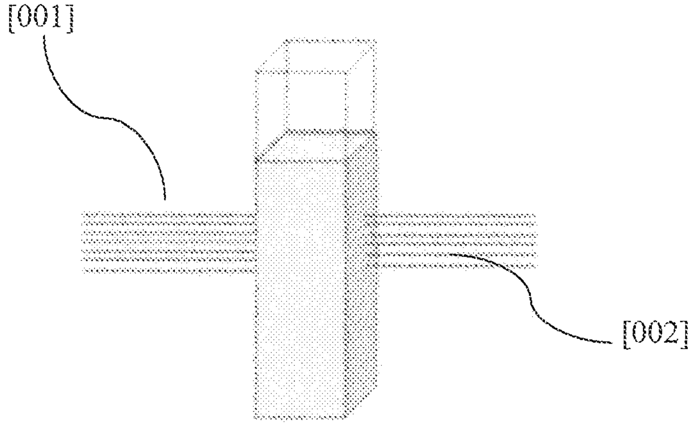
FIG. 2
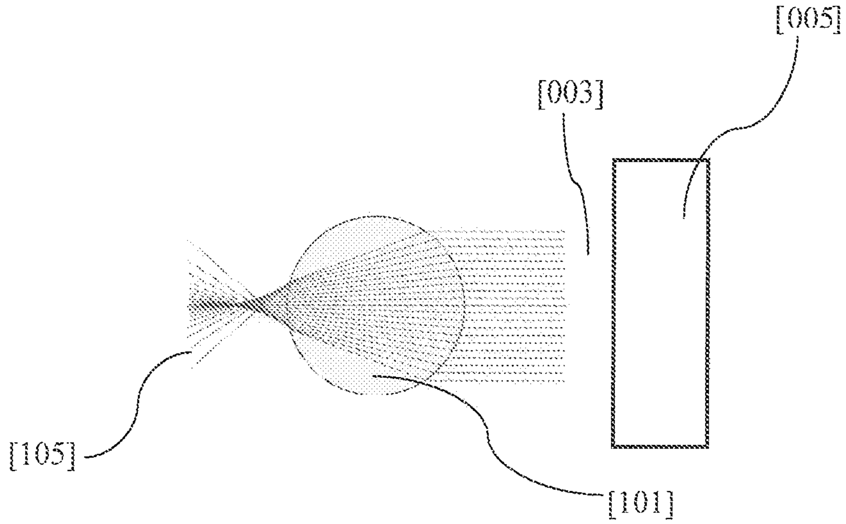

SPECTROPHOTOMETER BASED ON OPTICAL CAUSTICS

CROSS-REFERENCE TO RELATED APPLICATIONS

This application claims priority to and the benefit of U.S. Provisional Application Ser. No. 6172644 and U.S. application Ser. No. 13/987,658 the disclosures of which are expressly incorporated herein by reference in their entirety.

FIELD

Embodiments disclosed herein relate to spectrophotometers.

BACKGROUND

Accurately detecting the size and/or presence of particles is advantageous in many technologies and industries, including food processing, materials manufacturing, biotechnology, environmental, and medical testing. Measuring random changes in the intensity of monochromatic collimated light from a laser, which is scattered from a suspension or solution is a known technique for particle size distribution detection and changes in particle sizes or distribution during aggregation, dissolution, crystallization, or coagulation events. The currents state of the art optical instruments for measuring particle size include dynamic light scattering (DLS), photon correlation spectroscopy (PCS), nephelometry, and quasi-elastic light scattering (QELS). All of these techniques involve illuminating particles with monochromatic, collimated light and employ planar or cylindrical sample chambers between the source (a laser) and the detecting unit. In scattering media, the intensity of scattered light collected at different angles is a function of particle size, the wavelength of incident light, and the relative refractive index of the liquid or suspension medium and suspended particles. Laser light illuminates the sample that is enclosed in a sample chamber or cell, and the scattered light signal is collected with a detector placed at an angle with respect to the laser beam entering the sample chamber. However, the current state-of-the-art particle sizing technology is unable to utilize the presence of caustics. Some of the advantages that Applicants have discovered in the use of caustics in measuring particle size includes achieving faster results without the need for expensive sophisticated equipment (e.g., mirrors, lens, amplification, light splitting, monochromated light sources).

For example, in U.S. Pat. No. 7,268,874, a method of measuring properties of particles immersed in a body that includes performing a series of instantaneous acquisitions by illumination of the body with a temporally coherent light beam of predetermined width D and predetermined wavelength □ so that the light beam interacts with the particles by generating scattered radiation, and the detection of a plurality of values of the intensity of the total radiation. However, U.S. Pat. No. 7,268,874 fails to teach the use of caustics to focus light with droplet to form an optical caustic and amplify the light by droplet geometry as demonstrated in current invention. Many techniques known in the art simply do not suggest using caustics and instead require mirrors for re-emitting of light (as in U.S. Pat. Nos. 8,174,773, 7,187,441, and 5,815,611), the use of amplifiers (as in U.S. Pat. No. 6,796,195), special screening members (as in U.S. Pat. No. 8,123,040), or other expensive and sophisticated equipment. See U.S. Pat. No. 6,738,144 (teaching the use an interferometer for particle size determination); U.S. Pat. No. 5,627,642 (teaching the use of a length of a gradient index multimode optical fiber fusion spliced to a monomode optical fiber). Other techniques do not use optical caustics at all, either in catacaustic or diacaustic forms. See, e.g., U.S. Pat. No. 7,331,233 (teaching the use of ultrasound attenuation).

SUMMARY OF THE INVENTION

The scope of the present invention is defined solely by the appended claims, and is not affected to any degree by the statements within this summary. Disclosed herein are embodiments of an apparatus for particle size and a distribution of a population of particle measurements, comprising: a non-monochromatic light source that emits a plurality of a non-monochromatic, rays, a medium that includes a particle, wherein the medium is a liquid phase and the particle is suspended within the medium to form a particle-suspension, a droplet of the particle-suspension wherein the droplet is provided with a curved surface, and a detector that is provided with a light providing element.

BRIEF DESCRIPTION OF DRAWINGS

FIG. 2. Comparison between light rays passing through a rectangular cuvette compared to a spherical chamber. Path length of the cuvette is assumed to be 1 cm, while the diameter of the spherical chamber is 1 cm.

FIG. 10. (b) Data using a sample shaped to create an optical caustic with detection using a spectrometer with a diffraction grating. This illustrates that the deviation from the Beer-Lambert law is due to stray light from the detector and shows very good agreement with the cuvette measurements.

DETAILED DESCRIPTION OF THE PRESENTLY PREFERRED EMBODIMENT

In the disclosed invention, ordinary light is emitted through an air or gas medium and enters through a liquid sample that contains suspended particles in the fluid medium. The suspended particles include a nanoparticle solution or a mixture of nanoparticle and/or a molecule of interest. The liquid sample holder includes a contact lens, spherical glass shell, and/or surface that flows water to bead into a sphere. Due to the geometry of the drop shape, when the light exits the liquid medium it is refracted at the liquid/air interface and shaped, resulting in the formation of a diacaustic. By placing a detector at 180 degrees from the light source and centered at the paraxial focus, a high intensity region is detected and tracked as a temporal signal using a light collector (preferably selected according to the wavelength of light used as the source). It is within the scope of the present invention to select ordinary light generated from a plurality of lamps and sources, including photodiodes of a predetermined wavelength range (the wavelength of the source light being selected preferably according to the size of the particles being investigated and the path length to the detector window). The detector is a range of photon detectors, such as a photodiode or photo-detector, that generate a signal; the detector is selected according to the wavelength of light illuminating the sample. The diacaustic used to create a complex pattern of high and low intensity regions of light can be formed by a plurality of means [1]. Optical caustics formed from carved surfaces created by a spheroidal, toroidal, hemispherical, hyperboloidal, conical, ellipsoidal, or arbitrary droplet shape that produces Overlapping rays of light can be used. However, a spheroidal shape is preferred in order to have a simple alignment between the light source and detector. The temperature, pressure, ionic strength, surface tension, gravity, and molecular composition of medium can be varied to alter the shape of the optical caustic. The distance between the light source and light detector is dimensioned to capture the high intensity light flux region due to the paraxial focus. Particles of uniform size and composition in medium give a unique signal at a given sampling frequency and the signal can be attributed to size and composition. Mixtures of particle sizes cause a mixed light signal that provides data indicating the change in the overall particle population size. Data collection rates depend on the particle size range being studied, but can be standardized to commonly used frequencies for most technological applications.

Figure 1:
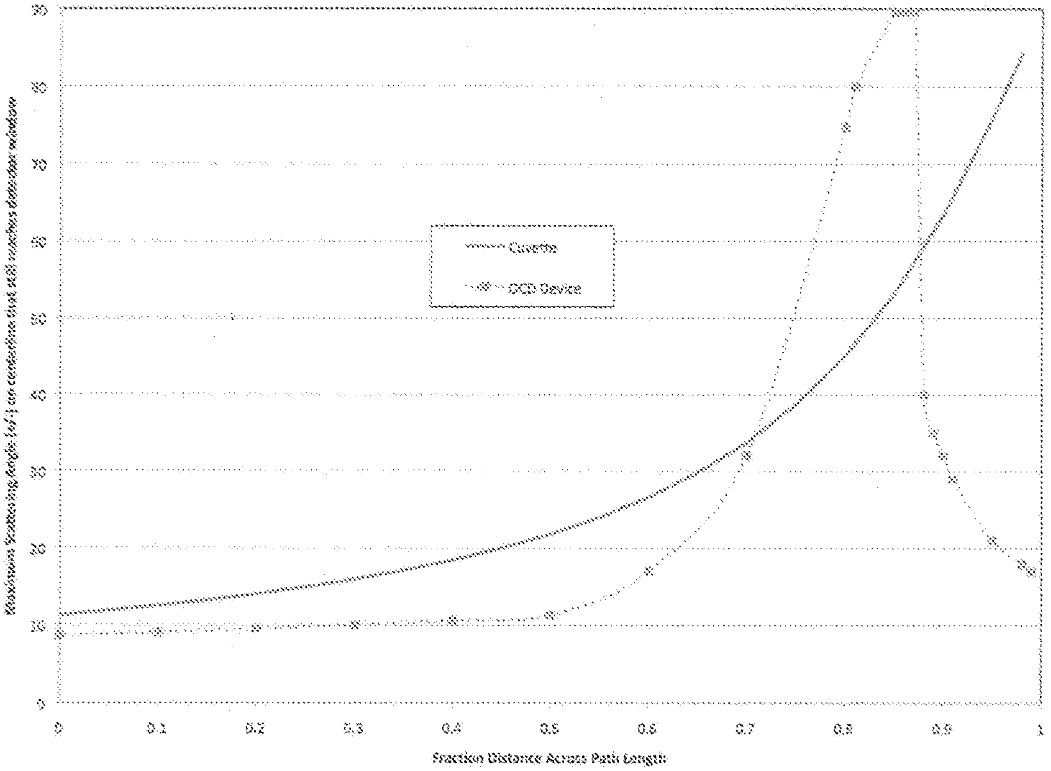
FIG. 1. The curves show the maximum possible angle that a ray of light can be scattered in order to detect light originating from the center of a cuvette versus for a spherical sample chamber that generates an optical caustic. For the cuvette the detector is placed at the wall of the cuvette while for the spheroidal sample the detector is 1 cm from the center of the sphere. The calculated data points for the drop are connected in order to make the trend easier to visualize.

In another embodiment, an apparatus for spectroscopy measurements, comprising a generally non-monochromatic light source that emits a plurality of non-monochromatic rays; a medium that includes a particle, wherein the medium is a liquid phase and the particle is suspended within the medium to form a particle-suspension; a droplet of the particle-suspension wherein the droplet is provided with a curved surface; a detector that is provided with a light providing element; the light source and droplet are oriented with respect to one another so that the rays of light travel from the light source though the droplet to form an optical caustic paraxial focus; and the droplet and the light-detecting element is located within 1.5 mm (as is illustrated in FIG. 1) of the optical caustic focus.

This invention exploits a difference between a sample placed in a standard rectangular or cylindrical cuvette container or cell, as compared to a holder shaped to provide an optical caustic, specifically for samples containing particles that scatter light. FIG. 1 illustrates this difference for a rectangular cuvette versus a spherical sample chamber. In FIG. 1, the curves indicate the maximum angle of scatter. In FIG. 2, the light (004) would still reach a detector positioned 180 degrees from the light source (005) for a ray that originates at die centerline of each of the two sample holders (001) and (105), respectively. The rectangular sample holder contains a liquid (preferably water with particles in suspension (002) and the spherical container or holder with a droplet that includes a particle suspended (101) in a fluid medium. While the presently preferred embodiment uses water, other embodiments use other liquids, such as alcohol and oils. For the cuvette, a path length of 1 cm in a gas or air medium (003) is assumed and a spherical container of 1 cm diameter (can be smaller or larger) is used in FIG. 2*a* to illustrate the differences using these containers. It is assumed that each device has a centered detector window of length 4 mm, and for the cuvette the window is placed at the end of the path length of the cuvette while for the sphere it is placed 1 cm from the center of the spherical sample container. Also, it should be noted that angles beyond the critical angle within the sphere lead to reflection, and those rays are considered to be undetected. In order to best analyze the effect of generating an optical caustic, the sample chambers are assumed to be very thin walled with a refractive index equal to that of the liquid sample.

The result of this geometric calculation for the cuvette is that when scattering occurs closer to the detector, the maximum scattering angle for light that can reach the detector increases. However, for the spherical sample chamber, at the liquid/air interface, refraction that creates the diacaustic can dramatically change the path of the light. The curves show that, based on ray tracing, detection of light scattered at between 80-90 degrees is possible within a window of between 0.8-0.85 of the fractional distance along the path length. Combining this with the comparison between the ray-trace of a spherical versus rectangular sample holder (FIG. 2), shows that light measurement using optical caustic detection for a sample droplet containing suspended particles is fundamentally different.

One advantage of this invention is that for the spherical chamber, the change in the measured light with dilution for a sample that only absorbs light is markedly different than that of a sample with particles that scatter light. This effect leads to a device that can determine the presence of scattering nanoparticles in a liquid sample droplet rather than a sample that contains dyes or other light absorbing molecular species. Conducting a one-step dilution in a standard cuvette positioned at 180 degrees from the light source does not provide this simple particle detection.

Another advantage of using diacaustics for measuring particle sizes is that microscopic patterns of high and low intensity described in the scientific literature [1-2] create a means by which fluctuations in the total light can be detected due to the relative size and hence relative speed at which particles within the sample move, based on the well-known Stokes-Einstein equation. Thus, ordinary light can be used since the caustic itself generates an interference pattern. The autocorrelation function, which is used to determine instrument parameters and sizes of unknown particles in samples, can then be applied for the detection of the diacaustic with the same goal of calibrating the system to track solid particle size changes with time or determine the static particle size distribution of a sample droplet.

The simple instrument design due to the optical caustic leads to the detection of changes in particle size of a sample in non-laboratory or field settings as a means of testing for a particular component in a sample. For example, in detecting viruses, antibodies or nucleic acids can be placed on nanoparticles and mixed with a sample with the intent that the nanoparticles will aggregate when a target viral protein or RNA is present in the sample.

Arbovirus detection is a major concern in public health since insects carry the viruses and have been spreading diseases in areas of the world that had not previously seen these types of diseases. One embodiment of the present invention is a field deployable instrument to detect arboviruses using a nanoparticles probe based on determining changes in particle size as a reliable and simple means for rapid testing. Optical caustic based technology is a digital platform for the early diagnosis of arboviruses; in such an embodiment, an optical caustic based analysis is used to detect arboviral diseases, infectious diseases, or other infection. Climate change has increased significantly the potential threat of arboviruses (World Health Organization, 2000). Optical caustic spectroscopy measurement is also used to help preventive mosquito population surveillance by identifying the quantity of mosquito eggs in a given sample of water. Developing countries are specially hit by high costs of public health prevention. Over the last 50 years, healthcare spend has outpaced CDP growth by about 2% a year in most OECD countries (OECD, 2011), so prevention (as opposed to cure) will be the way to go in the future. Early diagnosis is important in both developed and under developed countries. Thus, (1) Surveillance, (2) early diagnosis and (3) real-time transmission of information to healthcare providers minimizes further complications and thereby the mortality from these infections. Also, early detection decreases the efficiency of control strategies such as vector management, vaccination, and public awareness campaigns.

In another embodiment, the optical caustic based apparatus or instrument is used to determine the presence of a protein in biological samples, prescreen blood serum, medical assay, and environmental monitoring applications. In one embodiment, an apparatus or process, whereas, a non-monochromatic light source is provided. Light enters a medium 1 droplet that contains particles. Medium 1 droplet is mixed with nanoparticles and/or microparticles. The medium 1 droplet shape is modified by the container, medium 2, the surface that the medium droplet is placed on or a combination of these shape modifers. The light exiting the medium 1 droplet is modified by the geometric shape of medium 1 droplet. A detector is placed at 180 degrees from the light source. A detector is placed at the paraxial focus. Particles are detected by resultant signals with diluted samples. Particle sizes are determined by tuning sampling frequency range and analyzing time dependent signal. An optical caustic created by a spherical drop of Medium 2 is used; however, in another embodiment, an optical caustic created by a spheroidal drop of Medium 2 is used. In yet another embodiment, an optical caustic created by a toroidal drop of Medium 2 is used. In still another embodiment, an optical caustic created by a hemispherical drop of Medium 2 is used. It is within the scope of the present invention to use an optical caustic created by a hyperboloidal drop of Medium 2, an optical caustic created by a conical drop of Medium 2, an optical caustic created by an ellipsoidal drop of Medium 2, or an optical caustic created by an irregular Medium 2 shape (which produces an envelope of overlapping rays of light).

In another embodiment, the temperature of Medium 2 is varied to alter the shape of the optical caustic. The pressure of Medium 2 can be varied to alter the shape of the optical caustic. The ionic strength of Medium 2 can be varied to alter the shape of the optical caustic. The molecular composition of Medium 2 can be varied to alter the shape of the optical caustic. Particles of uniform size and composition in Medium 2 give a unique signal at a given sampling frequency and the signal can be attributed to size and composition. The time varying light detected generates information for a specific particle size distribution of interest. The detection of particle size changes can be used to detect target molecules in a sample. Mixtures of particle sizes cause a mixed signal that can be interpreted to determine the change in the overall particle population size.

In another embodiment, determining nano or microparticle sizes in a liquid suspension requires expensive instrumentation and calls for training, specialized software, and a laboratory to house and maintain the instruments and sample handling peripherals. Industrial (paint, food, pharmaceuticals), water testing, and nanotechnology research and school science laboratories measure particle suspensions for a variety of reasons such as quality control, monitoring changes in particle sizes, and characterizing their synthesized particle products. These users desire a simpler, low-cost; and portable system to provide useful information on particle size distributions.

The optical caustic product is a portable and low cost alternative that exploits communication device, phone, and Smart phone software for signal interpretation. The apparatus uses a optical caustic method and translates the electronic information directly into audible sound that can be interpreted by communication devices or phones using free or low cost applications to provide useful information on particle size distributions.

Spectrophotometer Based on Optical Caustics

In the disclosed invention, ordinary light enters a liquid sample that contains molecules that interact with light. Due to the geometry of the sample shape, when light exits the liquid it is refracted at the liquid/air interface and shaped, resulting in the formation of a diacaustic. By placing a detector at 180 degrees from the light source and centered at the paraxial focus, a high intensity region can be detected and tracked as a temporal signal using a light collector appropriate for the wavelength of light used as the source (see FIG. 2). Ordinary light can be generated from a variety of lamps and sources, including photodiodes of a particular wavelength range (0.001 nm to 750 nm), depending upon the sample being investigated. The detector can be a range of photon detectors that generate a signal (such as a photodiode or photo-detector) when suitably matched to the wavelength of light illuminating the sample. Alternatively, various detectors can be used such as diffraction gratings or diode arrays if wavelength-specific information is desired. The diacaustic used to create a complex pattern of high and low intensity regions of light can be formed by a variety of means [3], but a spheroidal shape is preferred in order to have a simple alignment between the light source and detector. The distance between the light source and detector is dimensioned to capture the high intensity light flux region due to the paraxial focus. Data collection can be a single value reading at a variety of wavelengths or collected over a period of time for kinetic studies. According to the invention the solid particles of signal-generation substances are crystals or amorphous particles or mixtures thereof. In a preferred embodiment of the invention the solid particles have a particle size from 10 nm to 100 μm, preferably smaller than 50 nm.

In another embodiment, a optical caustic process, whereas, a non-monochromatic light source is provided. Light enters a medium 1 droplet that contains molecules. The medium 1 droplet shape is modified by the container, medium 2, the surface that the medium droplet is placed on or a combination of these shape modifers. The light exiting the medium droplet is modified by the geometric shape of medium 1 droplet. A detector is placed at 180 degrees from the light source. A detector is placed at the paraxial focus. Molecules are detected by resultant signals with diluted samples. Molecule absorptions are determined by tuning sampling frequency range and analyzing time dependent signal. In further exemplary embodiments of the present invention, the solid particle added to the droplet included in the apparatus made therefrom, as described above, may comprise inorganic materials such as, for example, metals, metal compounds, metal oxides, semiconductive metal compounds, and/or carbon species such as carbon fiber, graphite, carbon black, fullerenes, or nanotubes. The solid particle may include particulate organic materials or fibers made of organic materials such as polymers, oligomers or pre-polymers, for example, a synthetic homopolymer or copolymer of an aliphatic or aromatic polyolefin, such as polyethylene or polypropylene; or a biopolymer.

In still further exemplary embodiments of the present invention, the solid particle added to the droplet included in apparatus as described above may comprise at least one inorganic material in combination with at least one organic material, or a combination of at least one particulate material with at least one material having a form selected from sphere, tubes, fibers or wires. In another exemplary embodiment of the present invention, the solid particle added to the droplet may be provided in the form of sphere, tubes, fibers or wires. In further exemplary embodiments of the invention, the solid particle added to the droplet includes materials such as, for example silica, titanium dioxide, metal particles, tantalum particles, or polyethylene particles; and the solid particle may comprise epoxy resins or phenoxy resins. A material used to form a solid particle or a portion thereof, or a coating thereon, may be obtained from a liquid mixture comprising at least one organic solvent, where the mixture may be solidified by removal of the solvent using, e.g., a heat treatment without decomposing the matrix material. Examples of other materials which may be used in conjunction with the solid particles materials described herein may include, for example, amorphous and/or (partially-) crystalline carbon, solid carbon material, porous carbon, graphite, carbon composite materials, carbon fibers, ceramics such as zeolites, silicates, aluminum oxides, aluminosilicates, silicon, carbide, silicon nitride, metal carbides, metal oxides, metal nitrides, metal carbonitrides, metal oxycarbides, metal oxynitrides and metal oxycarbonitrides of the transition metals, such as titanium, zirconium, hafnium, vanadium, niobium, tantalum, chromium, molybdenum, tungsten, manganese, rhenium, iron, cobalt, nickel; metals and metal alloys, in particular the noble metals such as gold, silver, ruthenium, rhodium, palladium, osmium, iridium, platinum; metals and metal alloys of titanium, zirconium, hafnium, vanadium, niobium, tantalum, chromium, molybdenum, tungsten, manganese, rhenium, iron, cobalt, nickel, copper; steel, in particular stainless steel, memory alloys such as nitinol, nickel titanium alloy, glass, stone, glass fibers minerals, natural or as well as any combinations of the aforementioned materials and/or combinations thereof with the solid particle material as described herein.

A solid particle may comprise organic and/or inorganic materials of any suitable form or size, or any mixtures thereof. For example, the solid particle(s) may include inorganic materials such as, for example, zero-valent metals, metal powders, metal compounds, metal alloys, metal oxides, metal carbides, metal nitrides, metal oxynitrides, metal carbonitrides, metal oxycarbides, metal oxynitrides, metal oxycarbonitrides, organic or inorganic metal salts, including salts from alkaline and/or alkaline earth metals and/or transition metals, including alkaline or alka alkaline earth metal carbonates, -sulfates, -sulfites, semi conductive metal compounds, including those of transition metals and/or metals from the main group of the periodic system; metal based core-shell nanoparticles, glass or glass fibers, carbon or carbon fibers, silicon, silicon oxides, zeolites, titanium oxides, zirconium oxides, aluminum oxides, aluminum silicates, talcum, graphite, minerals, phyllosilicates, or any mixtures thereof.

Solid particles may also be biodegradable metal-based compositions, for example, alkaline or alkaline earth metal salts or compounds such as magnesium-based or zinc-based compounds of the like; or nano-alloys or any mixture thereof. The solid particles used in certain exemplary embodiments of the present invention may include magnesium salts, oxides or alloys, which can be used in biodegradable coatings or molded bodies, and which can be provided in the form of an implant or a coating on an implant that may be capable of degradation when exposed to bodily fluids, and which may further result in formation of magnesium ions and hydroxylapatite.

Solid particles may also include, but are not limited to, powders, including nanomorphous nanoparticles; of zero-valent-metals, metal oxides or combinations thereof, e.g., metals and metal compounds which may be selected from the main group of metals in the periodic table, transition metals such as copper, gold and silver, titanium, zirconium, hafnium, vanadium, niobium, tantalum, chromium, molybdenum, tungsten, manganese, rhenium, iron, cobalt, nickel, ruthenium, rhodium, palladium, osmium, iridium or platinum, or rare earth metals. Metal-based compounds which may be used include, e.g., organometallic compounds, metal alkoxides, carbon particles such as, for example carbon fibers or diamond particles, and the like. Solid particles may also include metal-containing endohedral fullerenes and/or endometallofullerenes, including those comprising rare earth metals such as, e.g., cerium, neodymium, samarium, europium, gadolinium, terbium, dysprosium, holmium, iron, cobalt, nickel, manganese or mixtures thereof such as iron-platinum-mixtures or alloys. Magnetic super paramagnetic or ferromagnetic metal oxides may also be used including, e.g., iron oxides or ferrites, e.g. cobalt-, nickel- or manganese ferrites. Magnetic metals or alloys may be used to provide materials having magnetic, super-paramagnetic, ferromagnetic or signaling properties, such as ferrites, e.g. gamma iron oxide, magnetite or ferrites of Co, Ni, or Mn.

A solid particle can include any combination of materials listed herein. Additionally, semiconducting compounds and/or nanoparticles may be used as a solid particle added to the droplet in further exemplary embodiments of the present invention, including semiconductors of groups II-VI, groups III-V, group IV of the periodic system. Suitable group I-VI-semiconductors include, for example, MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, HgTe or mixtures thereof. Examples of group III-V semiconductors include, for example, GaAs, GaN, GaP, GaSb, InGaAs, InP, InN, InSb, InAs, AlAs, AlP, AlSb, AlS, or mixtures thereof. Examples of group IV semiconductors include germanium, lead and silicon. Also, combinations of any of the foregoing semiconductors may be used.

In certain exemplary embodiments of the present invention, it may be preferable to use complex metal-based nanoparticles as solid particles. The core of semiconducting nanoparticles having a core-shell configuration may have a diameter of about 1 to 30 nm, or preferably about 1 to 15 nm, upon which further semiconducting nanoparticles may be crystallized to a depth of about 1 to 50 monolayers, or preferably about 1 to 15 monolayers. Cores and shells be present in combinations of the materials listed above, including CdSe or CdTe cores, and CdS or ZnS shells.

In a further exemplary embodiment of the present invention, the he solid particle added to the droplet may be selected based on their absorptive properties for radiation in a wavelength ranging anywhere from gamma radiation up to microwave radiation, or based on their ability to emit radiation, particularly in the wavelength region of about 60 nm or less. By suitable selection of a solid particle, materials having non-linear optical properties may be produced. These include, for example, materials that can block IR-radiation of specific wavelengths, which may be suitable for marking purposes or to form bioassay radiation-absorbing markers. The solid particle, their particle sizes and the diameter of their core and shell may be selected to provide photon emitting compounds, such that the emission is in the range of about 20 nm to 1000 nm. Alternatively, a mixture of suitable compounds may be selected which is capable of emitting photons of differing wavelengths when exposed to radiation.

In one exemplary embodiment of the present invention, fluorescent metal-based compounds may be selected that do not require quenching. Alternatively, or in addition, the solid particles are provided it the form of tubes, fibers, fibrous materials or wires, including nanowires, which can comprise any of the materials mentioned above. Examples of such agents may include carbon fibers, nanotubes, glass fibers, metal nanowires or metal microwires. These solid particles can have an average length of about 5 nm to 1,000 μm, or about 5 μm to 300 μm, or preferably about 5 μm to 10 μm, or about 2 to 20 μm, and/or an average diameter between about 1 nm and 1 μm, about 1 nm to 500 nm, preferably about 5 nm to 300 nm, or about 10 to 200 nm.

In one embodiments, disease can be monitored for measuring particle size or concentration. Examples of the diseases include, acinetobacter infection, actinomycosis, African trypanosomiasis, AIDS, Amebiasis, Anaplasmosis, Anthrax, Arcanobacterium haemolyticum, Argentine hemorrhagic fever, Ascariasis, Aspergillosis, Astrovirus infection, babesiosis, bacillus cereus infection, bacterial pneumonia, bacterial vaginosis, bacteroides infection, Balantidiasis, Baylisacaris infection, BK virus infection, Black piedra, Bolivian hemorrhagic fever, Botulim, Brazilian hemorrhagic fever, Brucellosis, Burkholderia infection, Buruli ulcer, calicivirus, Norovirus, Sapovirus, campylobacteriosis, Candidiasis, cat-scatch disease, cellulitis, Chagas disease, chancroid, chickenpox, chlamydia, Cholera, chromoblastomysis, clonorchiasis, clostridium difficile, coccidioidonaycosis, Colorado tick fever, common cold, Creutzfeldt-jakob disease, Crimean-Congo hemorrhagic fever, Cryptococcosis, Crytosporidiosis, Cytomegalovirus, Dengue fever, Diphtheria, Ebola hemorrhagic fever, Echinococcosis, Epidemic typhus, Faciolosis, Glaciers, Hantavirus, Hepatisis Herpes, Hookworm, human metapneumovirus, HPV, influenza, keratisis, kuru, lassa fever, leishmaniasis, lyme disease, Malaria, Marburg hemorrhagic fever, mumps, Murine typhus, mycoplasma pneumonia, mycetoma, Myiasis, Norcadiosis, Onchocerciasis, Para gonimiasis, Pasteurellosis, Pediculosis corporis, Pediculosis pubis, Pertussis, Plague, Pneumocystid pneumonia, Q fever, Rabies, RSV, Rhinovirus infection, Rift Valley fever, rotavirus, Rubella, Salmonellosis, Scabies, Shingles, Syphilis, Tetanus, Tinea capitis, trichomoniasis, Tuberculosis, Venezuelan equine encephalitis, Venezuelan hemorrhagic fever, West Niles fever, White Piedra, Yellow fever, and Zygomycosis. These examples are not all exclusive.

Every modern biotechnology commercial, research, and educational laboratory measures fluorescence because it is a highly sensitive method to detect PCR products, proteins, cells, and is flexible for a wide range of biological techniques. Currently, fluorescence instruments acid detectors are very expensive and come with their own system to collect and manage data. Laboratories see limited access to the instruments as barriers to their work, but because of cost and resources needed to operate and maintain fluorescent measurement instruments, most labs share one instrument in a central location.

The optical caustic fluorimeter system is aimed at putting a fluorescence measurement system on every bench top by using optical caustic technology integrated with a do-it-yourself format. With this optical caustic system, combined with any communication device or phone can be used to take a picture of the fluorescent light from a sample using the two-step, optical caustic fluorimeter system. The acquired optical caustic image combined with a control picture or analyzed further to generate a line spectra.

Definitions

Arbovirus: Arbovirus is a term used to refer to a group of viruses that are transmitted by arthropod vectors. Some arboviruses are able to cause emergent disease. Any of a large group of RNA viruses that are transmitted primarily by arthropods, such as mosquitoes and ticks. The more than 400 species were originally considered to be a single group, but are now divided among four families: Togaviridae, Flaviviridae, Bunyaviridae, and Arenaviridae. These viruses cause a variety of infectious diseases in humans, including Rubella, Yellow Fever, Malaria, West Nile Virus, and Dengue Fever.

Optical Caustics: In differential geometry and geometric optics, a caustic is the envelope of rays either reflected or refracted by a manifold. It is related to the concept of caustics in optics. The ray's source may be a point (called the radiant) or infinity, in which case a direction vector must be specified.

Diacaustic: A curved formed by the consecutive intersections of rays of light refracted through a lens.

Paraxial focus: In the formation of an optical caustic, rays of light that arrive at a point are paraxial rays whereas other rays diverge. The point of convergence of the paraxial rays is past the circle of least confusion and is referred to as the paraxial focus.

Circle of least confusion: The smallest area where rays of light from a lens converge is known as the circle of least confusion. It is an optical spot caused by a cone of light rays from a lens not coming to a perfect focus when imaging a point source. It is primarily used in photography to determine the depth of field.

Fringe patterns: are interference fringes formed by the interference of monochromatic and coherent light to form visible dark and bright fringes. Fringe localization is the region of space where fringes with reasonably good contrast are observed.

Nanoparticle: In nanotechnology, a particle is defined as a small object that behaves as a whole unit in terms of its transport and properties. Particles are further classified according to size in terms of diameter, coarse particles cover a range between 10,000 and 2,500 nanometers. Fine particles are sized between 2,500 and 100 nanometers. Ultrafine particles, or nanoparticles are sized between 100 and 1 nanometers.

Catacaustic: A caustic formed by refraction of light is a catacaustic.

Autocorrelation function: Autocorrelation is the cross-correlation of a signal with itself. Informally, it is the similarity between observations as a function of the time separation between them. It is a mathematical tool for finding repeating patterns, such as the presence of a periodic signal which has been buried under noise, or identifying the missing fundamental frequency in a signal implied by its harmonic frequencies. It is often used in signal processing for analyzing functions or series of values, such as time domain signals.

Brownian motion: Brownian motion is among the simplest of the continuous-time stochastic (or probabilistic) processes, and it is a limit of both simpler and more complicated stochastic processes. This universality is closely related to the universality of the normal distribution. In both cases, it is often mathematical convenience rather than the accuracy of the models that motivates their use. This is because Brownian motion, whose time derivative is everywhere infinite, is an idealized approximation to actual random physical processes, which always have a finite time scale.

The term "nucleic acid," as used herein may include an oligonucleotide, nucleotide, or polynucleotide, and fragments thereof, and to DNA or RNA of genomic or synthetic origin which may be single- or double-stranded, and represent the sense or antisense strand, to peptide nucleic acid (PNA), to small interfering RNA (siRNA) molecules, or to any DNA-like or RNA-like material, natural or synthetic in origin.

Antisense gene: an antisense gene is constructed by reversing the orientation of the gene with respect to its promoter so that the antisense strand is transcribed.

Antisense RNA: an RNA molecule complementary to a particular RNA transcript that can hybridize to the transcript and block its function.

The term "functional equivalent," as used herein generally refers to a protein or nucleic acid molecule that possesses functional or structural characteristics that is substantially similar to a heterologous protein, polypeptide, enzyme, or nucleic acid. A functional equivalent of a protein may contain modifications depending on the necessity of such modifications for the performance of a specific function. The term "functional equivalent is intended to include the "fragments," "Mutants," "hybrids," "variants," "analogs, "" or "chemical derivatives" of a molecule.

The term "solid particle" as used herein may include an nanoparticle, mixed particles, inorganic particles, organic particles, and mixtures thereof.

The term "infection" as used herein may include any viral, fungal, and bacterial or mixture thereof.

Example 1. Optical Caustic and Traditional Light Measurement of Copper

One embodiment of the invention is illustrated by comparing the signal for a cuvette and spectrometer versus a sample shaped into an optical caustic when diluting a sample droplet containing a light-absorbing molecule versus a sample containing nanoparticles of Gold. For a light absorbing species such as a complexed copper ion in water, the intensity of light measured using a spheroidal liquid sample droplet at different dilution levels is compared to the standard means of measuring absorbance (Table 1). The measured values for the cuvette and spheroidal samples are in voltages read from a photo-detector that has a typical standard deviation in the reading of 4% (i.e., water is used as a reference). Water is also used as a reference for the spectrometer readings given in this table. The spectrometer reading is based on an average signal from 50 scans, while the cuvette and spheroidal drop readings are based on an average of multiple readings of a single number. Upon dilution, each method yields values that essentially follow the Beer-Lambert

TABLE 1

Absorbance readings for copper chloride solutions. The same cuvette was used in the spectrometer and the device. Values shown are for effective path lengths of 1 cm path length for two different concentrations.

| Sample | Spectrometer (640 nm) | Cuvette (no caustic) | Spheroidal sample (caustic) |
|---|---|---|---|
| Original Conc. | 0.35 | 0.37 | 0.37* |
| 50% Dilution | 0.19 | 0.22 | 0.23* |

*Since the drop is a spheroid about 6 ram in diameter, the values were adjusted to a 1 cm path length measurement.

Table 1. Absorbance readings for copper chloride solutions. The same cuvette was used in the spectrometer and the device. Values shown are for effective path lengths of 1 cm path length for two different concentrations. *Since the drop is a spheroid about 6 mm in diameter, the values were adjusted to a 1 cm path length measurement.

Example 2. Optical Caustic and Traditional Light Measurement of Gold Nanoparticle However, when detecting gold nanoparticles, which scatter light, there is a marked difference between the cuvette and spheroidal sample values, in Table 2, data for 10 nm gold particles as received from the vendor and diluted with distilled, deionized water are listed when using a near ultraviolet wavelength light emitting diode (LED) paired with a detector that collects light from this LED (primarily at 400 nm) and for a pair of 640 nm light emitting diodes (see Table 2.) For the spherical sample, chromatic aberration is significant causing a difference in the shape of the optical caustic at the detector so that a 300% higher intensity of light reaches the detector compared to the cuvette (measured against the signal with a DI water droplet), while there is a 70% increase in the intensity for the 640 nm LED. This difference helps explain the much higher optical density measured with the droplet using the near ultraviolet wavelength (e.g., Near UV) system since refraction at the paraxial focus at the surface of the droplet where light exits dominates the signal. Due to plasmon resonance, there is a high extinction of light, and it is dependent on particle concentration. When both cuvette and spheroidal drop are diluted to a level of 29%, the extinction of light in the Near UV system yields similar values.

| LED | Original Sample | Spectrometer | Cuvette with Device (No Caustic) | Spheroidal Sample with Device (Caustic) |
|---|---|---|---|---|
| Near UV | Original Conc. | 0.60 (400 nm) | 0.58 | 0.73* |
| Near UV | 29% Dilution | | 0.42 | 0.42* |
| Near UV | 55% Dilution | 0.36 (400 nm) | | |
| Red | Original Conc. | 0.11 (640 nm) | 0.11 | 0.13* |
| Red | 29% Dilution | | 0.076 | 0.12* |
| Red | 55% Dilution | 0.066 (640 nm) | | |

Table 2. Optical Density (Extinction) readings for 10 nm gold at different wavelengths and concentrations. The same quartz cuvette was used in the spectrometer and the device. *Since the drop was a spheroid of about 6 mm diameter, the values were adjusted to a 1 cm path length measurement.

For the 640 nm LED system, the optical density readings are similar for the cuvette with photodiode detection and for the cuvette using a spectrometer. However, since the optical caustic is wider due to chromatic aberration, the optical density reading is very insensitive to nanoparticle concentration and, in this case, remains nearly at the same value. This result shows that at two different wavelengths, changes in the reading for particles that scatter light differ markedly than for a standard cuvette measured using a spectrometer or using a simple photodiode detector. By comparing results from a cuvette and optical caustic upon dilution of the sample, this example teaches that the presence of particles that scatter light can be quickly established using this invention.

Example 3. Particle Size Determination of Polystyrene Spheres

Figure 3:
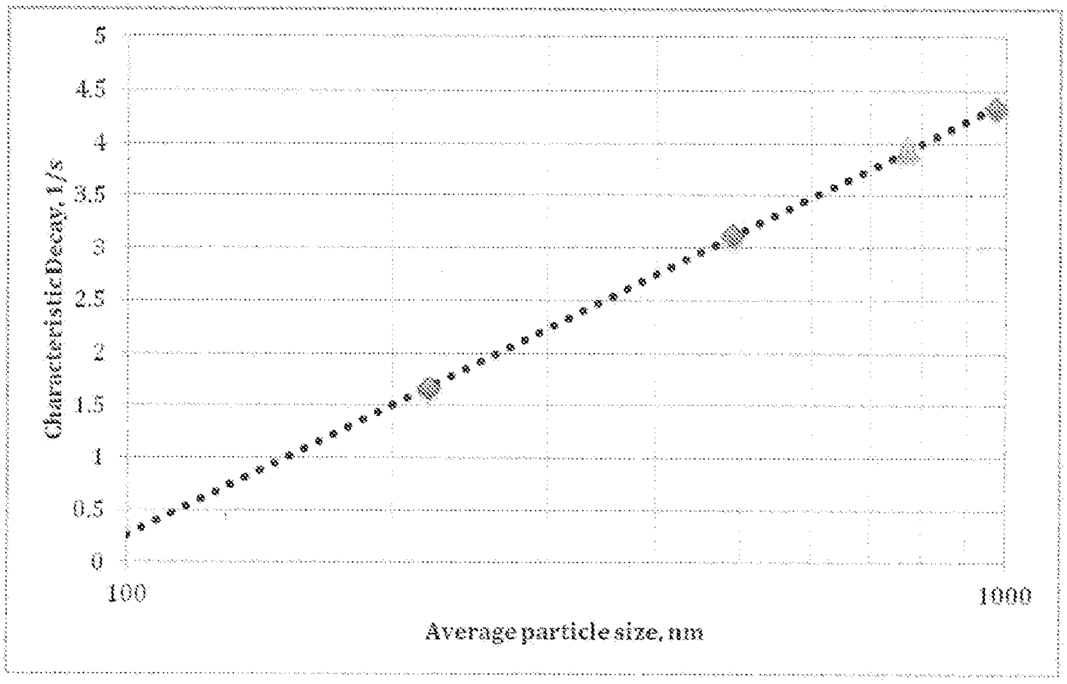
FIG. 3. Decay time versus particles size calibration data (diamonds), best-fit line for calibration (dashed line), and test sample (triangle) results using an optical caustic. Suspensions of particles at 220, 489, and 974 nm average diameter were used at different concentrations were to generate the calibration line through an analysis of the variation of light using an autocorrelation function. The data for this calibration was collected at 100 Hz. A sample containing 770 nm average particle size was measured using the same procedure and analyzed with the same autocorrelation function.

The optical caustic system generates time dependent data that can be analyzed to distinguish particle size in liquid. FIG. 3 is a calibration of data based on autocorrelation regression of charged polystyrene spheres of 200 (average, 220) nm, 500 (average, 489 nm), and 1,000 (average, 974) nm nominal diameter for the spheroidal sample droplet using an optical caustic. Sample concentrations measured for 200 nm spheres were 3.8x1010-1.1x1011 particles/ml for 500 nm spheres were 2.4x109-7.3x109; and for 1,000 nm spheres were 3x108-9x108 particles/ml. Samples were collected at 100 Hz and compared to a spheroidal sample droplet of water in order to establish that the time variation in the signal was due to the presence of particles. The decay frequency was determined after sampling 60 characteristic times and measuring the change in amplitude of the autocorrelation function for the three different particle sizes. To determine the average particle size based on the calibration, a fourth charged particle sample of 750 nm nominal (average, 770) particle diameter at a concentration of 5x109 was measured. The decay frequency for the fourth sample was determined to be 3.96, using the autocorrelation function graphing procedure used in the calibration. Based on the calibration plot, the average particle size was calculated to be 785 nm, which is within 2% of the average size based on the manufacturer's measurement.

Example 4. Metal Nanoparticle Droplet Detection Technology

Figure 4:
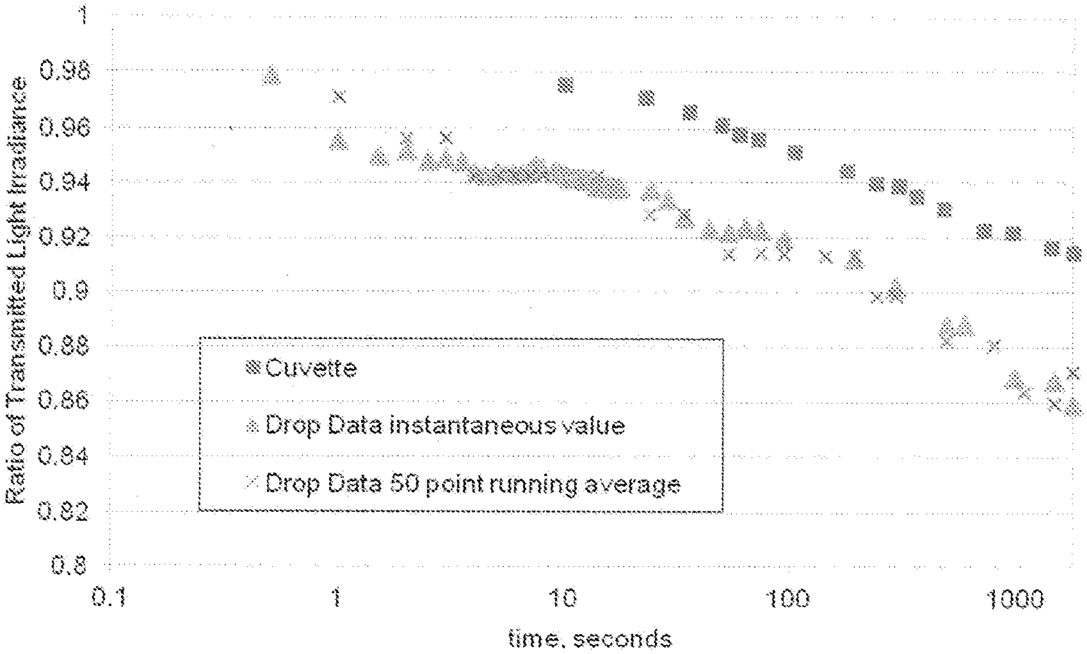
FIG. 4. The drop system yield aggregation signal changes faster than a cuvette. The rate of change in the cuvette follows diffusion-limited kinetics, while the drop appears to have at least three kinetic regimes.
Figure 5:
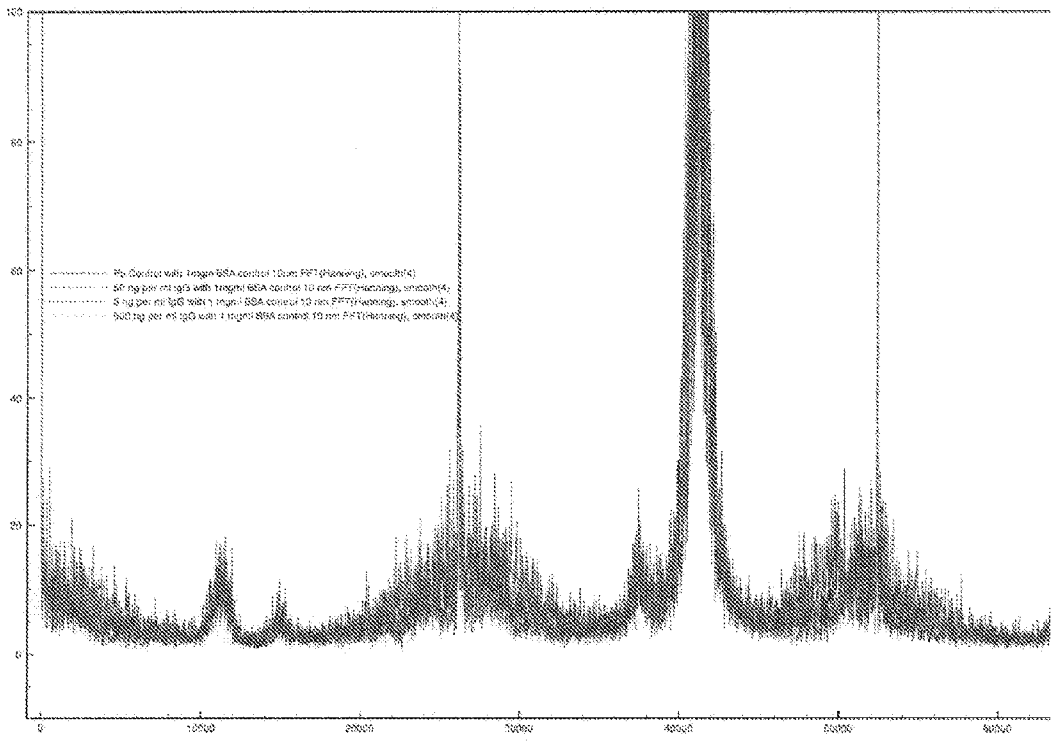
FIG. 5. A FFT power spectra series of antigen concentration (0.5 ng/ml, 50 ng/ml, 500 ng/ml) using 10 nm particles incubated with 1 mg/ml BSA in phosphate buffer as a control series.
Figure 6:
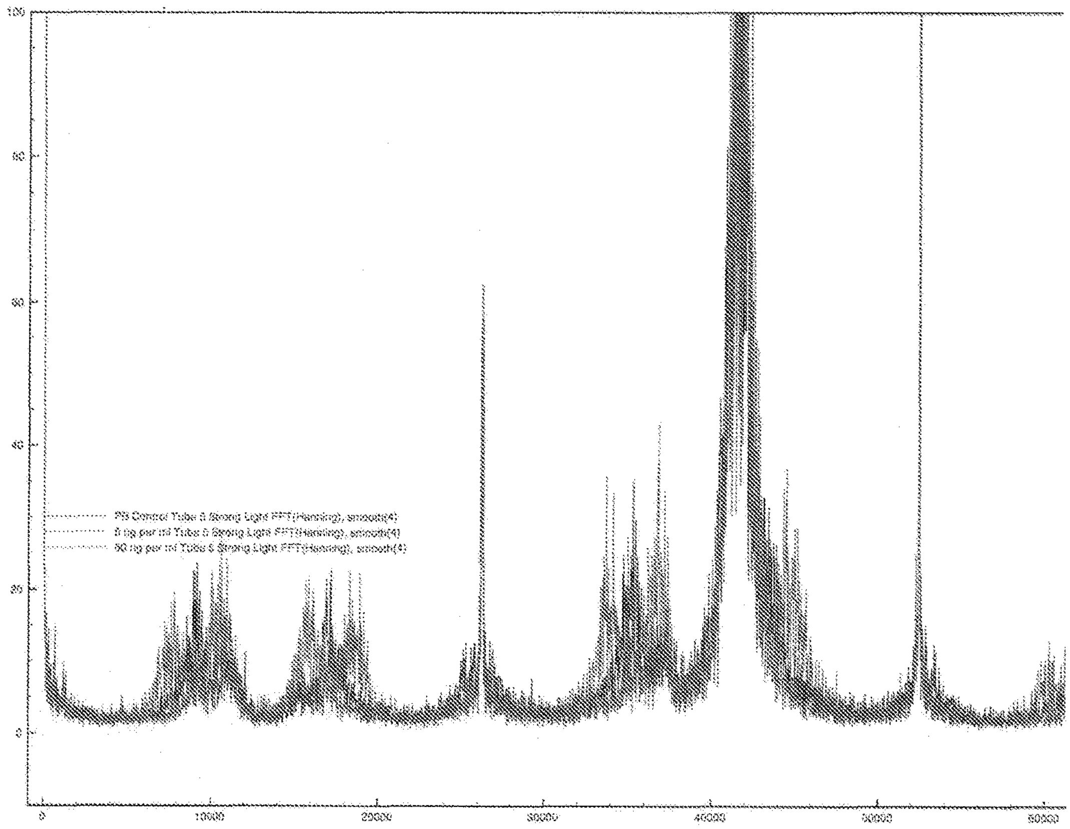
FIG. 6. A FFT power spectra series using 10 nm gold particles with anti-Human IgG antibody bound and suspended in 1 mg per ml BSA in phosphate buffer. There are regions where each data set shows peak separations. An instrument is used with a very strong LED (red, 620 nm).
Figure 7:
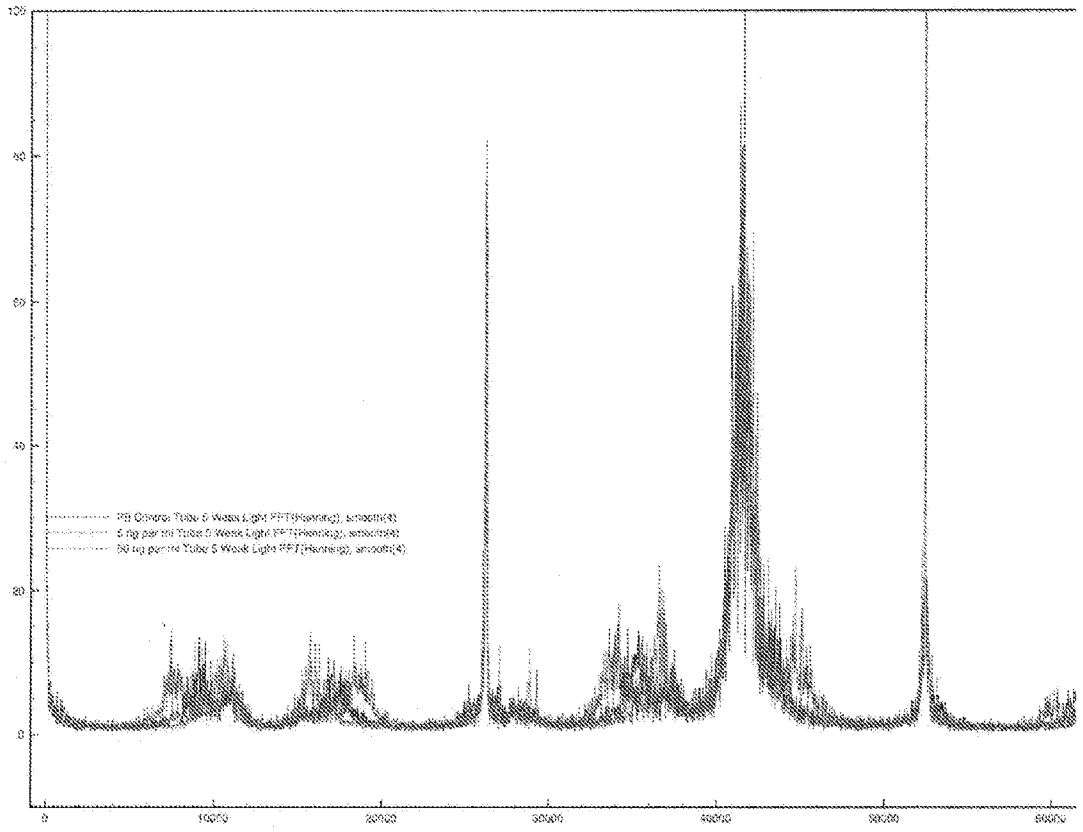
FIG. 7. A FFT power spectra series using 10 nm gold particles with anti-Human IgG antibody bound and suspended in 1 mg per ml BSA in phosphate buffer. There are regions where each data set shows peak separations. A different instrument is used with a weaker LED (red, 620 nm)
Figure 8:
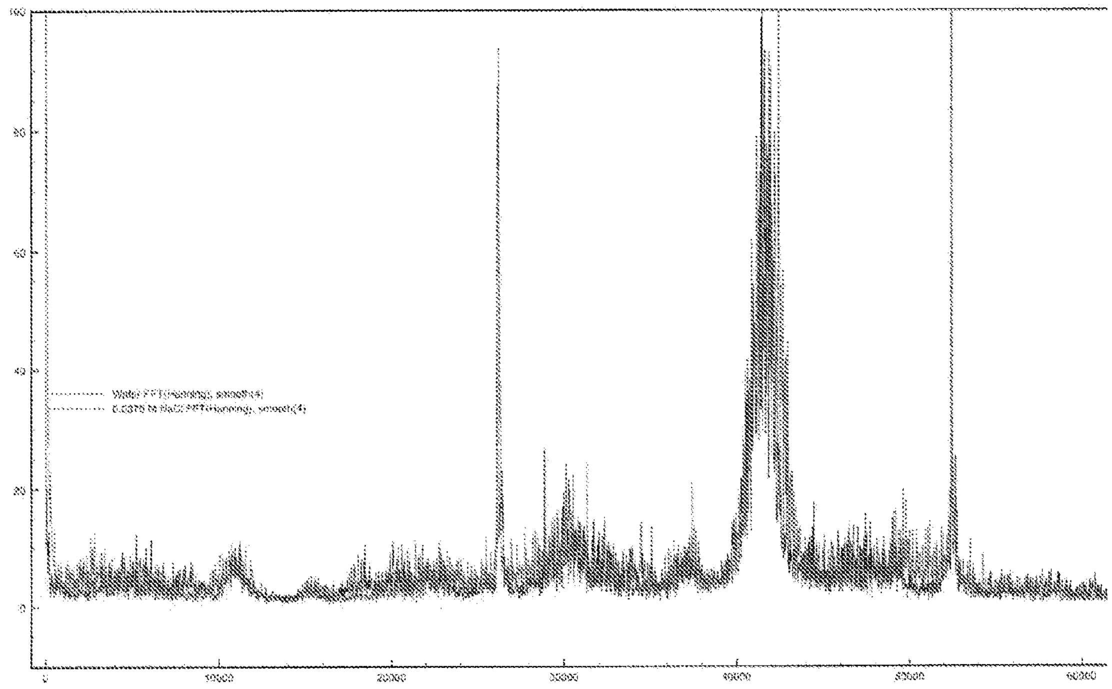
FIG. 8, Experiments with 10 nm gold from the bottle in water and 0.0375 M NaCl shows different power spectrum, but some aspects more similar to FIG. 5 rather than FIG. 6.

The "slow" aggregation of 10 nm gold particles due to low concentration of NaCl has been well studied and is a useful system to understand how detection using optical caustics in a droplet differs from standard cuvette measurements using a spectrometer for detection. Using photodiodes with peak transmittance/detection at 630 nm for the droplet device and a fiber optic UV/VIS spectrometer cuvette, "slow" aggregation using 0.0375 M NaCl was measured with data displayed in the FIG. 4. Spectrometer data was collected at 17 ms with 50 scan averaging to improve signal to noise ratio (S/N). The drop device data is displayed based on an instantaneous average value from a datalogger at 100 Hz and averaging the 50 points collected every half-second. The plot below shows the ratio of transmitted light irradiance using the irradiance of water and the 10 nm gold suspension as the irradiance at t=0. Because drops dry slowly, the water drop values at a specific time are used in this kinetic analysis in order to isolate the aggregation signal from other effects.

The cuvette data at 620 nm is plotted in the graph since it is the part of the spectra known to track well with slow aggregation. The time scale is given in logarithmic form in order to better display the data. After 10 seconds, the irradiance ratio for the droplet device reaches 0.94 while in the spectrometer this level is reached at a time of 300 seconds, indicated that within the droplet device, aggregation events are detected faster.

From a signal perspective, the rate appears to be faster by at least an order of magnitude presumably due to the self-organization of nanoparticles with clusters being crowded away from the surface of the droplet and free nanoparticles moving more easily towards the part of the droplet where evaporation takes place, thus increasing the frequency of collisions with other nanoparticles or clusters This analysis is relevant to the immunoassays in one sense because aggregation will be a useful signal to track at higher antigen concentrations. Typical concentrations detected using a spectrometer is at micrograms per ml of this antigen (Human IgG). But, there articles where a more elaborate system can track nanogram per ml levels. At these lower antigen concentrations there will be diffusion-induced changes of aggregates that will be more easily tracked using autocorrelation functions of intensity changes of a laser spot on one portion of the cuvette. The droplet device data can be easily interpreted using Fast Fourier Transformation (FFT). FIGS. 5-8 show that antibody bound to 10 nm particles can detect the antigen at least to 5 ng per ml levels. The ability of measuring ng per ml to pg per ml would be of high interest and make this a viable alternative to ELISA techniques. The combination of an optical caustic measurement with a droplet containing nanoparticles and a specific antigen or combination of antigens is capable of obtaining faster detection at the nanogram level then an ELISA technique.

Example 5. Food Coloring Blue Dye Optical Caustic Absorbance

Figure 9:
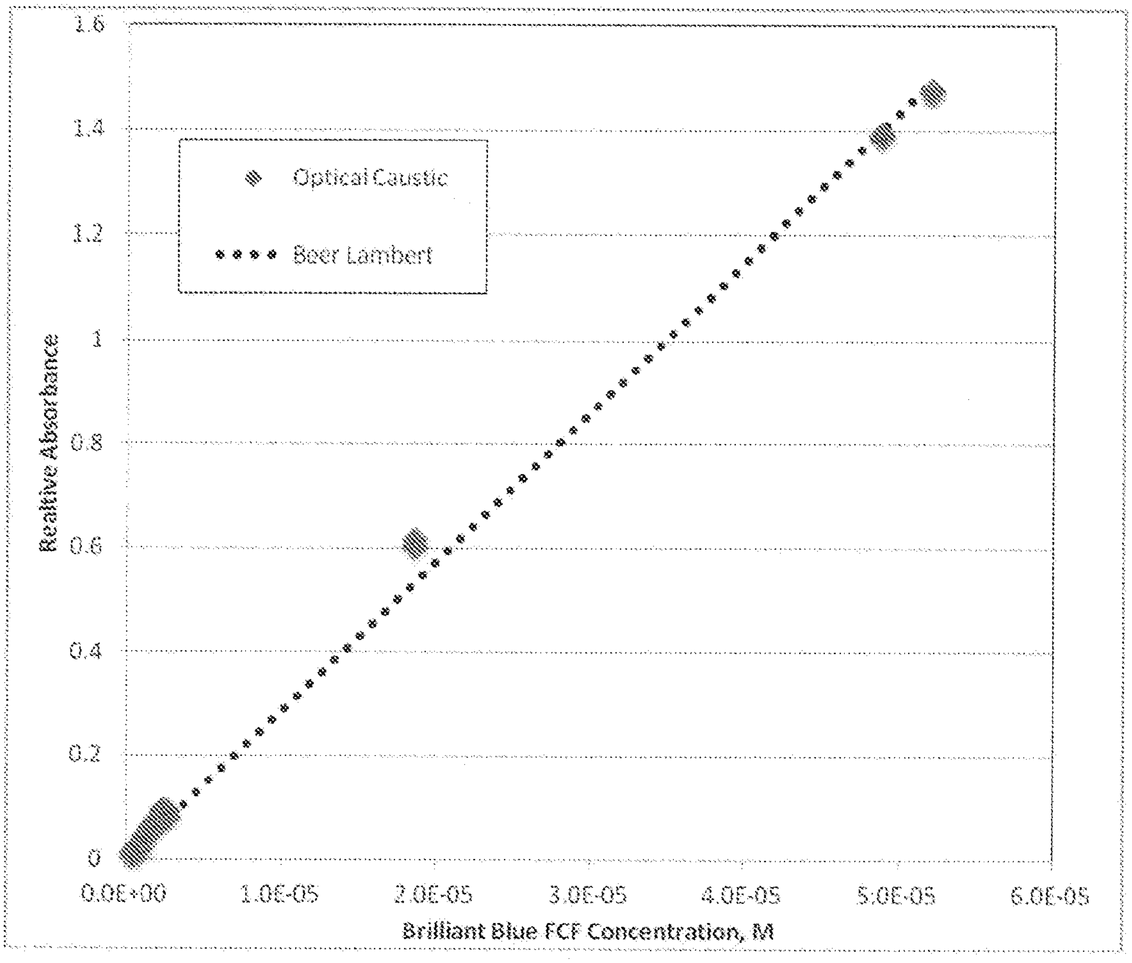
FIG. 9. Measurement of absorbance using a sample chamber that shapes a solution of Brilliant Blue to form an optical caustic when illuminated by light from a red LED (maximum at 630 nm). Absorbance follows a linear dependence with dye concentration even at high concentration.

One embodiment of the invention is illustrated by measuring the absorbance of light for the food coloring Blue Dye #1 (Brilliant Blue FCF) as a function of concentration using a spherical optical caustic (FIG. 9) as compared to measurements with a spectrophotometer. Blue #1 is a colorant for foods, has a color index of 42090, is soluble in water, and exhibits a maximum absorption at 628 nm. Using an optical caustic generated by a photodiode with emission between 620-640 nm and a matched photodiode as a detector, a wide concentration range is seen to be linear with absorbance for a spherical sample of 120 microliters (approximately 6 mm diameter). A water droplet is used as a reference and each data point represents triplicate measurements of the voltage reading from a photodiode detector amplified using a standard Op Amp circuit familiar to anyone skilled in the art of photodiode detector technology. The Beer-Lambert law fits the data well giving a r2 value of 0.998 for this instrumentation that employs a spherical sample geometry to generate an optical caustic (see FIG. 2 for an illustration of the caustic focus).

Figure 10A:
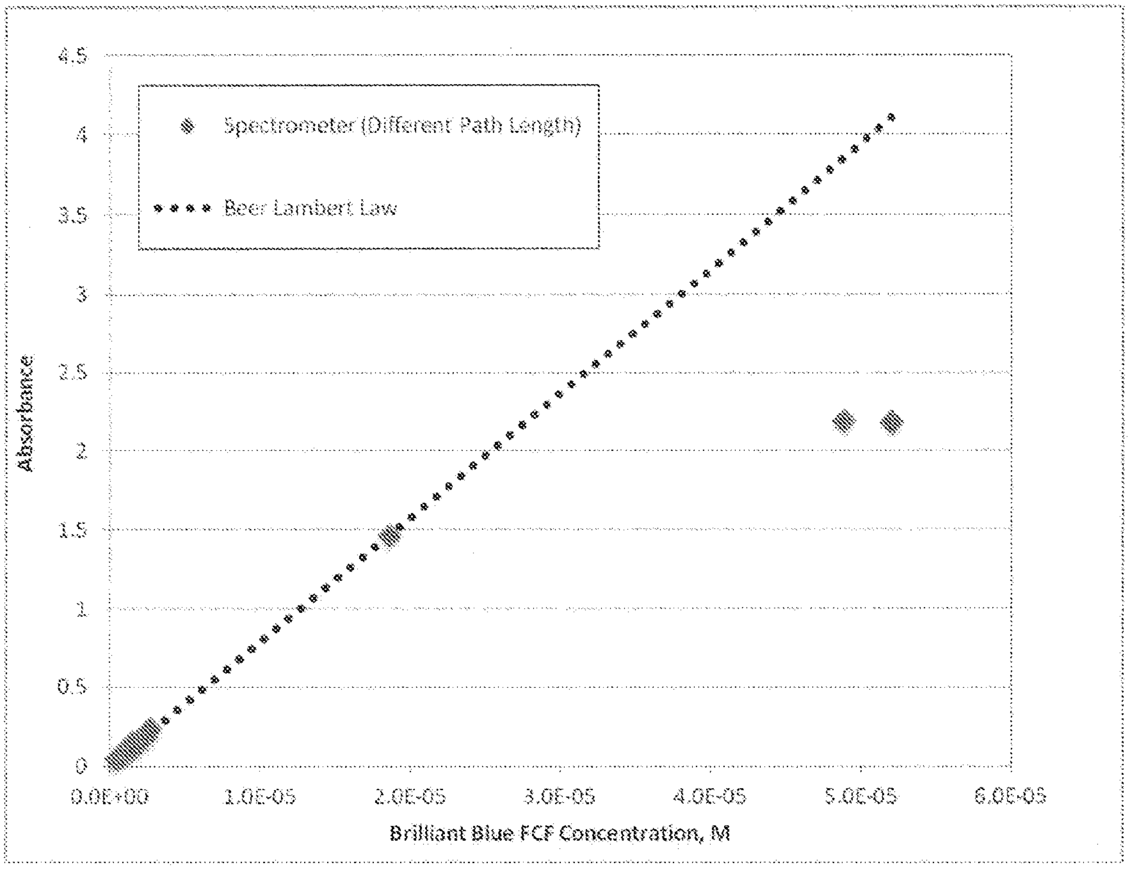
FIG. 10. (a) Brilliant blue absorbance versus concentration measured at the absorbance maximum using a spectrophotometer and a rectangular cuvette. Deviation from Beer-Lambert law is seen at absorbance above 1.5 using a 1 cm path length.
Figure 10B:
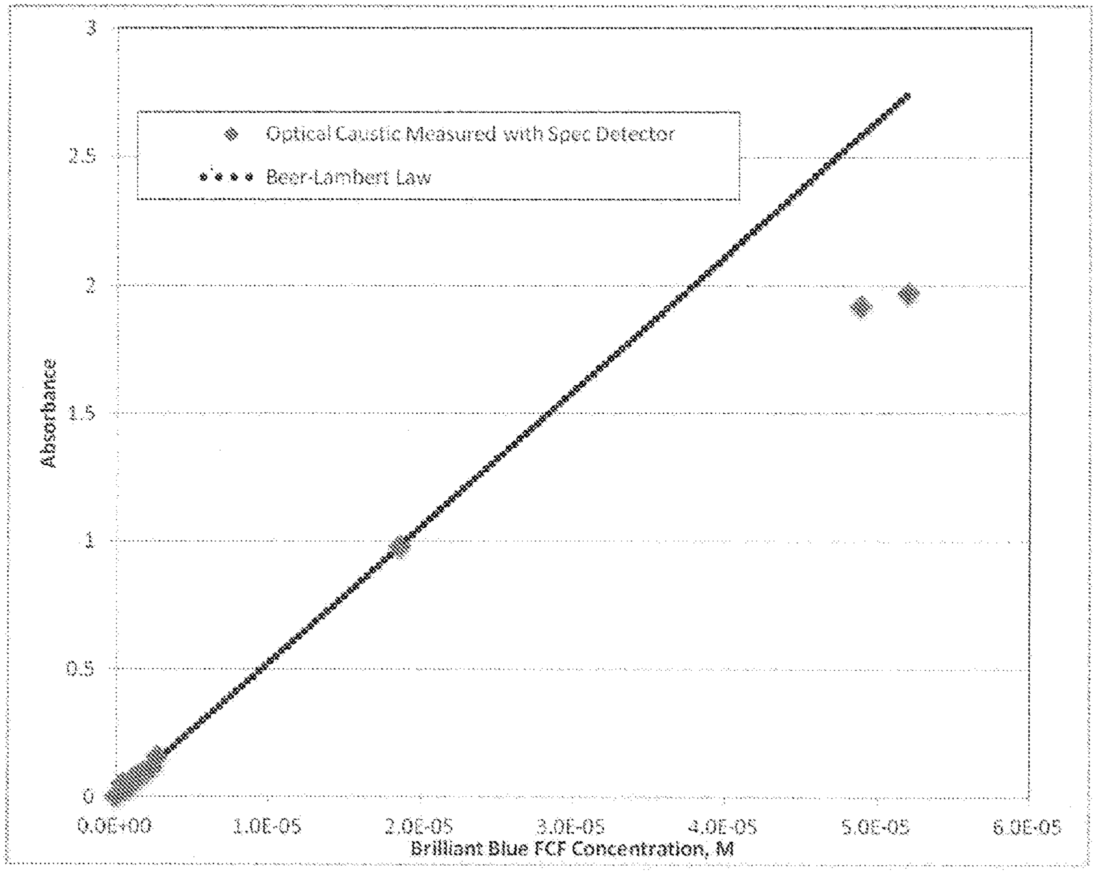

In FIG. 10, data using a spectrophotometer of path length 1 cm employing via software an average of 50 scans at 20 milliseconds per scan follows Beer Lambert law at concentrations below 20 micromoles per liter, but deviates significantly from this equation at concentrations above 40 micromoles per liter. This deviation from Beer-Lambert law linear dependence is well known to occur when absorbance exceeds a value of about 1 and is primarily attributed to stray light. In FIG. 10*b*, the data shows combining the shaping of the sample to create an optical caustic with a diffraction grating detector gives a deviation from Beer-Lambert law at higher concentrations of Brilliant Blue, indicating that stray light is likely the source of the deviation.

What this example teaches is the unobvious result that measuring the light focused into an optical caustic while being absorbed due to a molecule dissolved in the liquid medium gives a method to more accurately measure high absorption samples without resorting to dilution to measure higher concentration samples. The invention does not use a lens, mirrors, or costly optical emitter and detector systems in order to achieve a wider range of concentration measurement. While the linearity of the spectrophotometer readings may be improved through stray light correction strategies, the detection of very low light intensities and proper compensation requires more sophisticated and costly detection and lens systems.

Example 7 Food Coloring Yellow Dye Optical Caustic Absorbance

Figure 11:
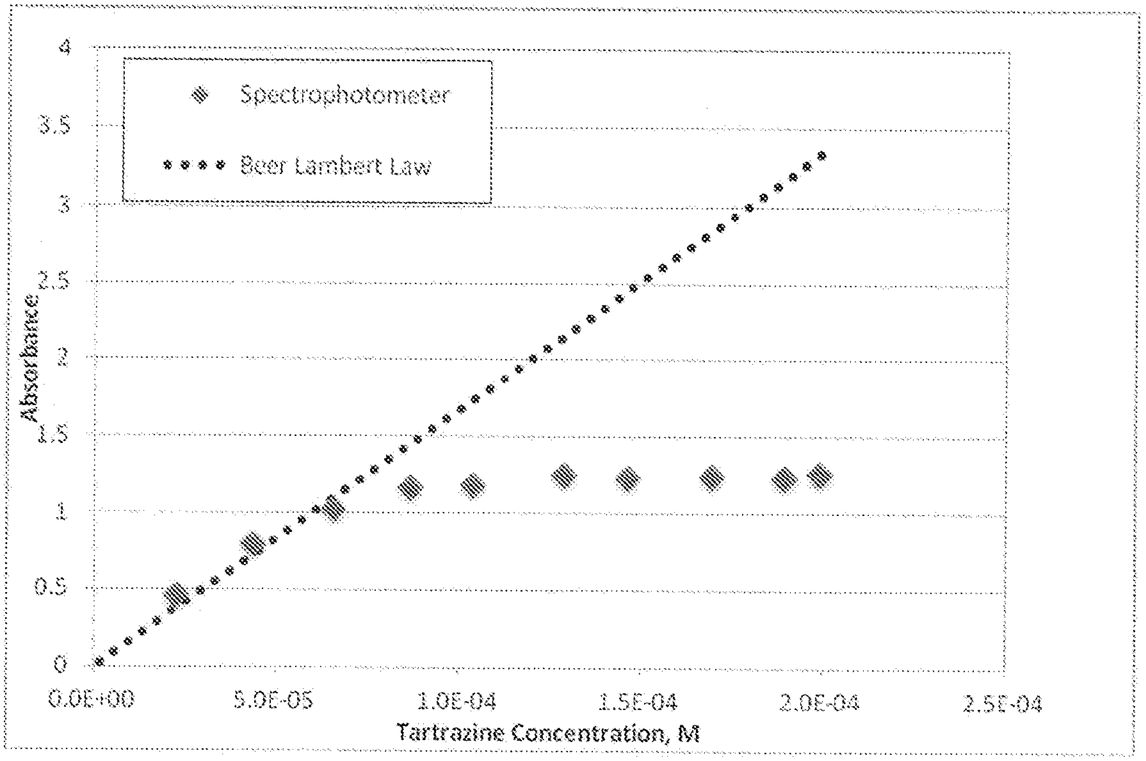
FIG. 11. Tartrazine (Yellow Dye #5) absorbance versus concentration measured at the absorbance maximum using a spectrophotometer and a rectangular cuvette, Deviation from Beer-Lambert law is seen at absorbance above 1.0 using a 1 cm path length.

Another embodiment of the invention is illustrated by measuring the absorbance of light for the food coloring Yellow Dye #5 (tartrazine) as a function of concentration in water using a spherical optical caustic (FIG. 11) as compared to measurements using a spectrophotometer (FIG. 11). Tartrazine has a color index of 19140, exhibits a maximum absorption at 427 nm, and fluoresces using excitation at a wavelength range of 350-450 nm with an emission peak between 500-750 nm. Using an optical caustic generated by a photodiode with peak intensity at 430 nm and a detector with a range between 400-500 nm, at concentrations below 0.1 mM absorbance the graph of absorbance versus concentration is seen to be linear using an optical caustic created by a spherical sample of 120 microliters (approximately 6 mm diameter), while for the spectrophotometer the Beer-Lambert law is valid for concentrations below 0.065 mM tartrazine (FIG. 11) which corresponds to Absorbance below 1. Water is used as a reference droplet and each data point represents triplicate measurements of the voltage reading from the photodiode, amplified by an Op Amp circuit.

Figure 12:
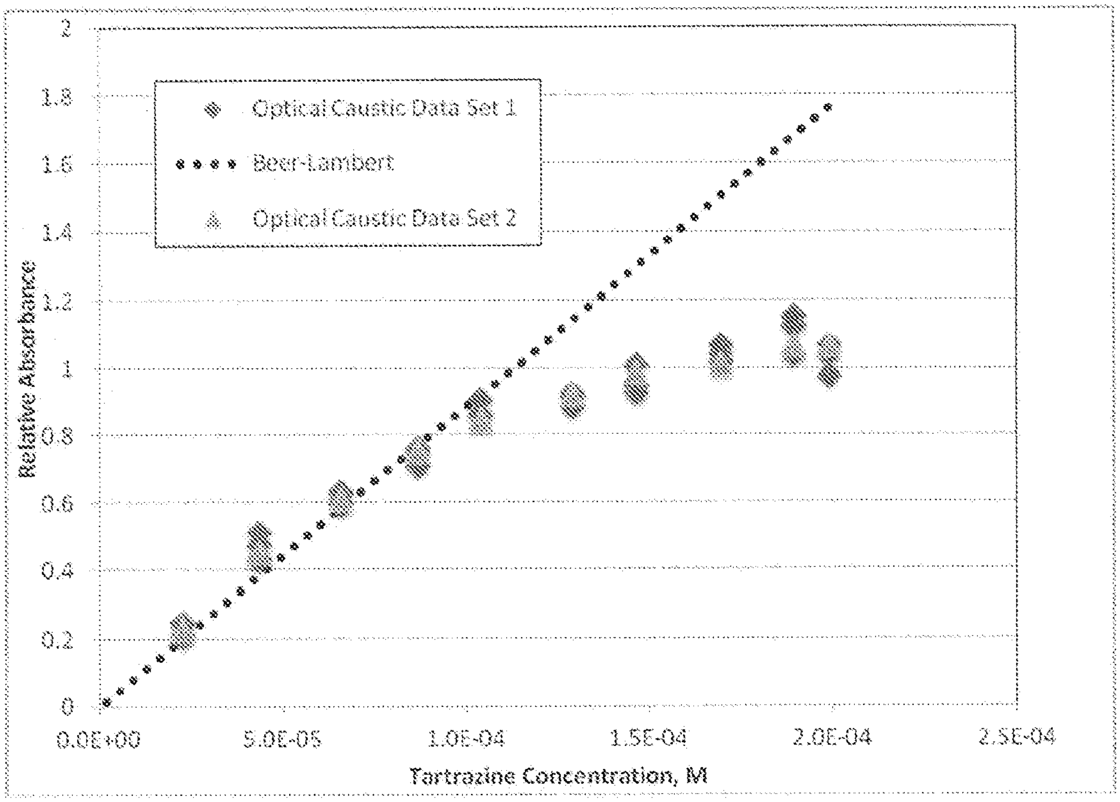
FIG. 12. Measurement of absorbance using a sample chamber that shapes a solution of Tartrazine to form an optical caustic when illuminated by light from a Blue LED (maximum at 430 nm). Absorbance follows a linear dependence until an absorbance of 0.8 is reached. However, the deviation from the Beer-Lambert law is due to the significant emission of fluorescence at concentrations above 0.1 mM tartrazine.

However, due to the additional light interaction of tartrazine molecules via fluorescence, the readings for the optical caustic differ fundamentally from the spectrophotometer. The intensity of light from the spectrometer is too low to generate fluorescence even at the highest concentration of tartrazine measured, and thus the deviation from Beer-Lambert law for the spectrophotometer and quartz cuvette is likely due to stray light. FIG. 11 illustrates absorbance spectra at the concentrations measured, and it exhibits a shape in agreement with published literature measurements. However, using the optical caustic and a Blue LED with intensity in the UV range, the sample emits green light at concentrations above 0.1 mM, which coincides with the deviation from the Beer-Lambert law (FIG. 12). Example 13 explores the measurement of tartrazine fluorescence from the sample shaped to generate an optical caustic.

Thus, this example illustrates the use of a different wavelength of light for absorbance measurement that the previous example with the additional feature of an indication that there is an additional mechanism for light interaction due to the deviation from an expected linear relationship between concentration and absorbance using an optical caustic.

Figure 13:
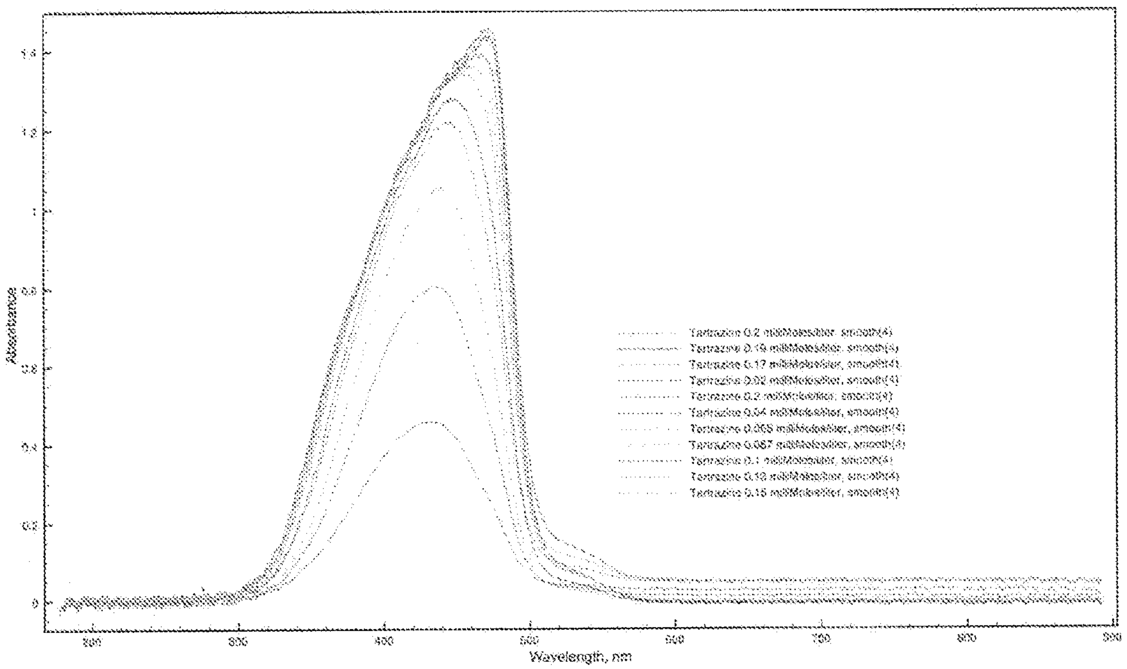
FIG. 13. A series of absorbance spectra for 11 concentrations of tartrazine using a spectrophotometer and a quartz cuvette of path length 1.0 cm. Fluorescence is not detected due to the light used for illuminating at UV wavelengths being at too low of an intensity.
Figure 14:
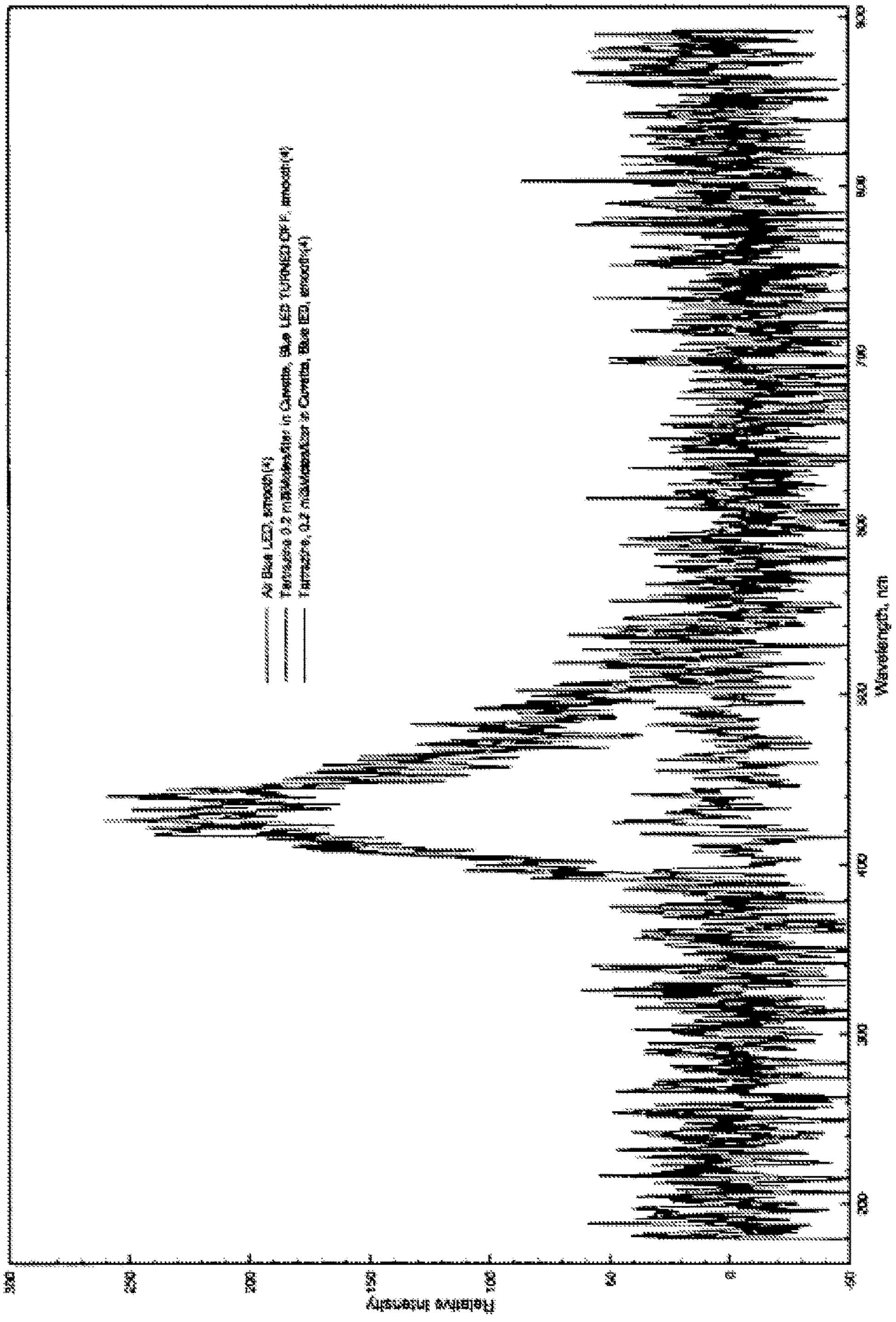
FIG. 14. Black line is the spectrometer reading of the Blue LED in air placed directly in line with the fiber optic detector. The blue line shows the intensity of light transmitted through a quartz cuvette, which is only slightly decreased in intensity. The red line shows the detector reading when the UV LED is turned off with the cuvette in front of the detector window.
Figure 15:
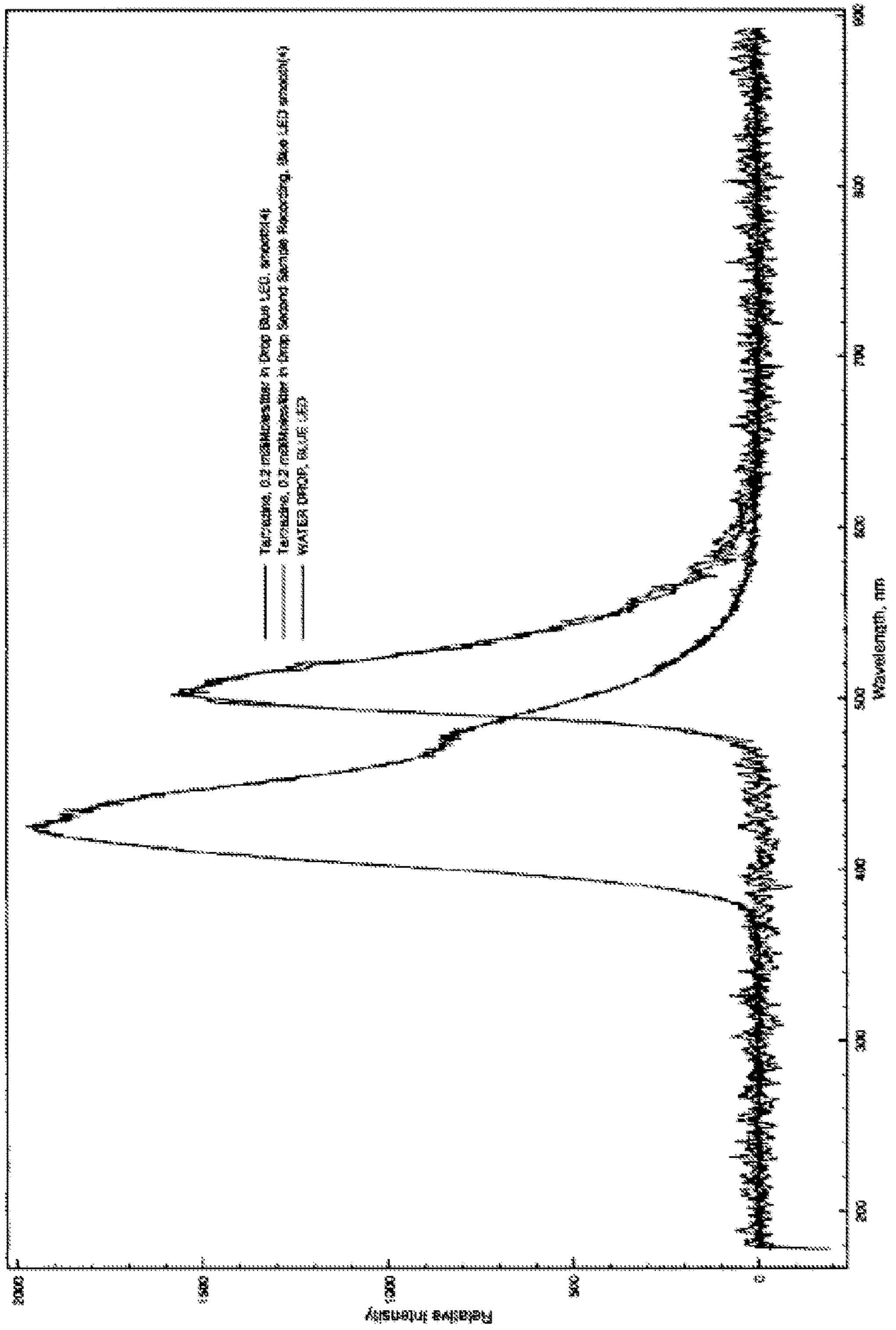
FIG. 15. Blue LED result with water and tartrazine drops. The optical caustic effect concentrates the intensity of the light and results in emission at 0.2. mM tartrazine to the extent that the excitation wavelength does not appear as a part of the spectra. The water drop result shown can vary 2-3 times higher, but this level of intensity is shown as a reference since it is easier to show the difference between the excitation wavelength range and the emission from tartrazine.

Example 8. Transition from Fluorescent to Other Light Interaction Mechanisms The intensification of light due to focusing within the sample leads to fluorescence measurement of tartrazine. In FIG. 14, a Blue LED is used as a light source and a spectrometer detector consisting of a fiber optic and diffraction grating is employed to measure the intensity of light transmitted through a quartz cuvette containing tartrazine at 0.2 nM concentration. No fluorescence is detected with a quartz cuvette, as shown in FIG. 13 for a range of tartrazine concentrations, but an increase in absorbed light is noticeable. However, when the sample is shaped into an optical caustic and the paraxial focus is centered on the detector lens, fluorescence emission is clearly detected at a concentration of 0.2 mM tartrazine (FIG. 15) at the same intensity of light incident to the sample droplet as for the quartz cuvette. FIG. 15 also gives a water droplet transmitting the Blue LED light, but the optical caustic is not centered completely at the detector lens in order to compare the wavelength of the tartrazine sample emitted light in FIG. 15 with the wavelength of the excitation source. It understood by those skilled in the art that fluorescence is proportional to the light intensity and, at low concentration, proportional to the concentration of the fluorescing molecule. At lower concentrations of tartrazine, some light from the emitter will also be measured along with the emission spectra. At the concentration illustrated in FIG. 13 and at higher concentrations, the excitation light does not appear in the measurement of light leaving the sample.

This example illustrates how adjusting the concentration of a fluorescent component in a medium combined with the intensification of the excitation light using an optical caustic, leads to a photonic measurement beyond where absorbance is the only mechanism for light interaction. The optical caustic-based spectrophotometer can achieve a level where fluorescence dominates the light reading thus simplifying this type of Measurement. Also, this example illustrates how a relatively weak light source can be amplified to a level sufficient to serve as a fluorescence excitation source.

Example 9. Brilliant Blue FCF (FD&C Blue No. 1) Optical Caustic Spectroscopy The optical caustic device can be used to measure absorbance of light at different wavelengths. In order to take into account the increase in light intensity within the optical caustic, the equation for light absorbance needs to be modified. The intensity of light can assume to change linearly within the sample chamber as a reasonable approximation.

$$dI=-\sigma NI dx+\alpha I_o dx$$

where I is the intensity of light at some point in the path length x, sigma is the coefficient for light absorbance, N is the number of molecules, a is a constant, and Io is the intensity of light entering the sample chamber.

If the constants are collected to create a dimensionless group defines as $$\beta = \frac{\alpha}{\sigma N}$$

this equation can be solved and put into a form resembling the Beer-Lambert Law where the term sigma*N is replaced with the familiar molar absorptivity, path length for a planar cuvette, and concentration. This equation reduces to the Beer-Lambert Law when beta equals 0. If the path length is zero, the equation also conforms to this boundary condition.

This equation can be used to determine how the observed absorbance in a caustic where the intensity changes linear with x is related to the Beer-Lambert Law based on prior knowledge of molar absorptivity or calibration with a spectrometer.

$$\left(\frac{I}{I_o}\right)_{observed} = \beta + (1-\beta)\left(\frac{I}{I_o}\right)_{Beer\text{-}Lambert}$$

Because the refractive index changes very slightly with wavelength of light beta will only be weakly dependent upon the wavelength of light used.

The example illustrate the utility of the optical caustic as a spectrophotometer and how fitting the equation to the Beer-Lambert Law provides a means of determining the concentration of a light absorbing substance at higher concentrations than using a standard cuvette.

Brilliant Blue FCF (FD&C Blue No. 1)

Figure 16:
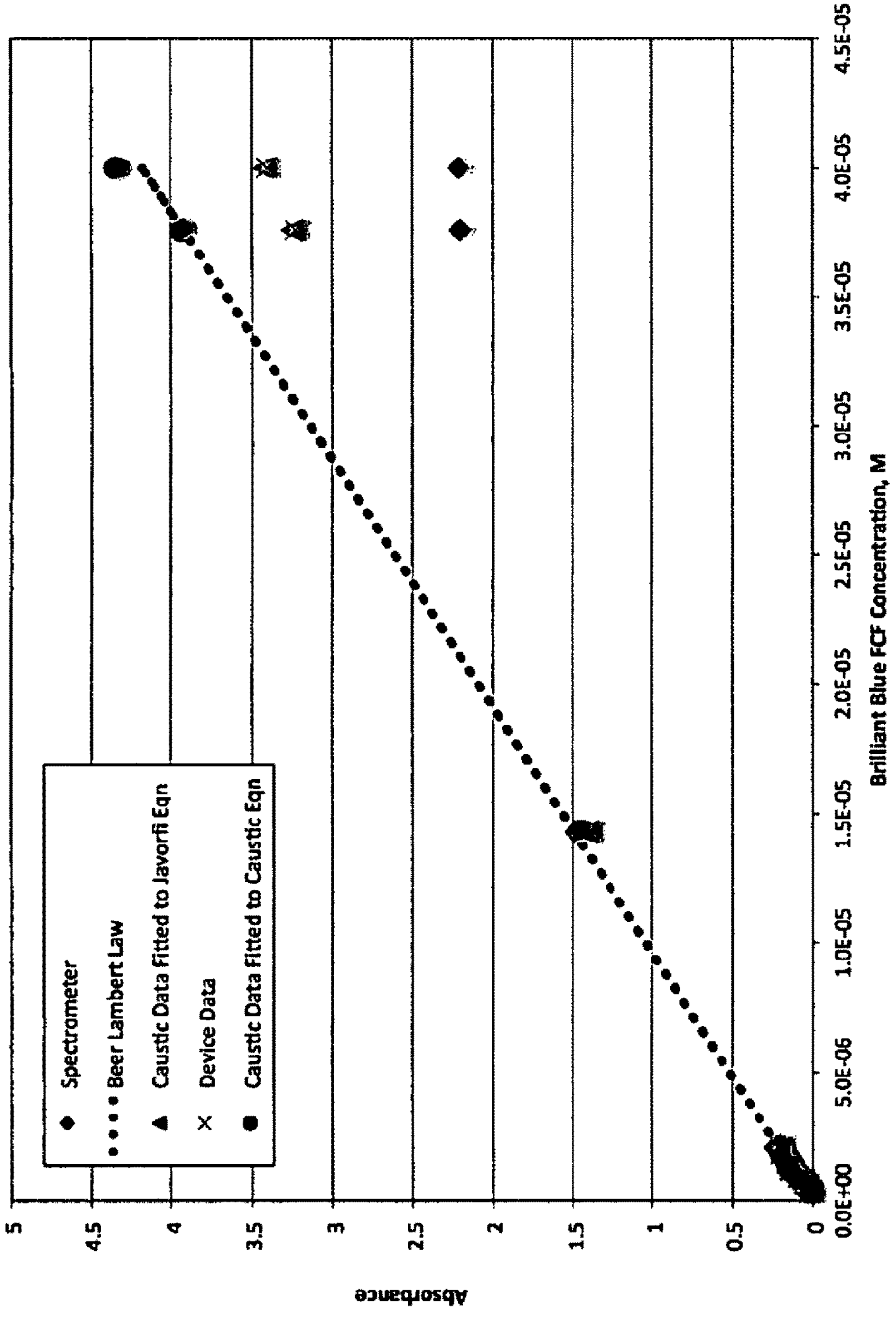
FIG. 16. Brilliant Blue FCF compared with Caustic Fitting and Beer Law
Figure 17:
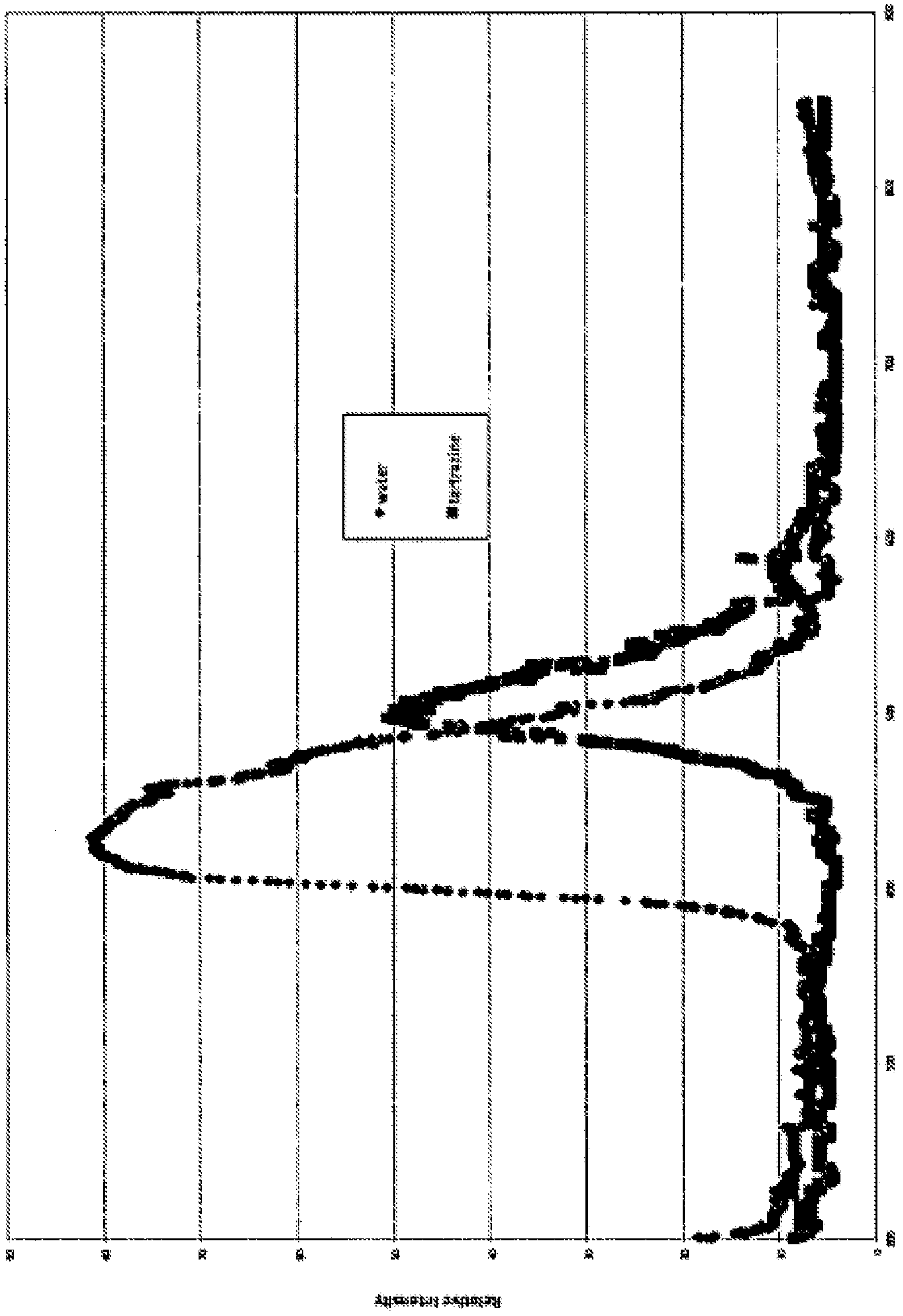
FIG. 17. Tartrazine and water droplet results and spectrometer.

This food dye has a very high color index with a maximum absorbance at 628 nm. Using photodiodes with a maxima at this wavelength, data was obtained using a spectrometer and the optical caustic device for 10 different concentrations. FIG. 16 shows this data along with corrections based on the work of Javorfi for an integrating cavity [7]U of Photochemistry and Photobiology, 2006 127-131 Vol 82] and the equation specific to an optical caustic linear increase in light intensity.

The data for the optical caustic are the average of triplicate runs. The spectrophotometer was ran in triplicate samples, but each data point is an average of 50 scans at 20 ms per scan.

The Caustic equation provides an excellent fit and allows the device to measure higher concentrations of dye as compared to a spectrophotometer. The ability to extend the Beer-Lambert Law to absorbance >1 allows for a wider range of measurement for highly concentrated solutions. The Caustic equation fit is an r2 value of 0.999 and a value for beta of 0.02 units.

Example 10. Optical Caustic Based Phone Fluorimeter Results with Tartrazine

Figure 18:
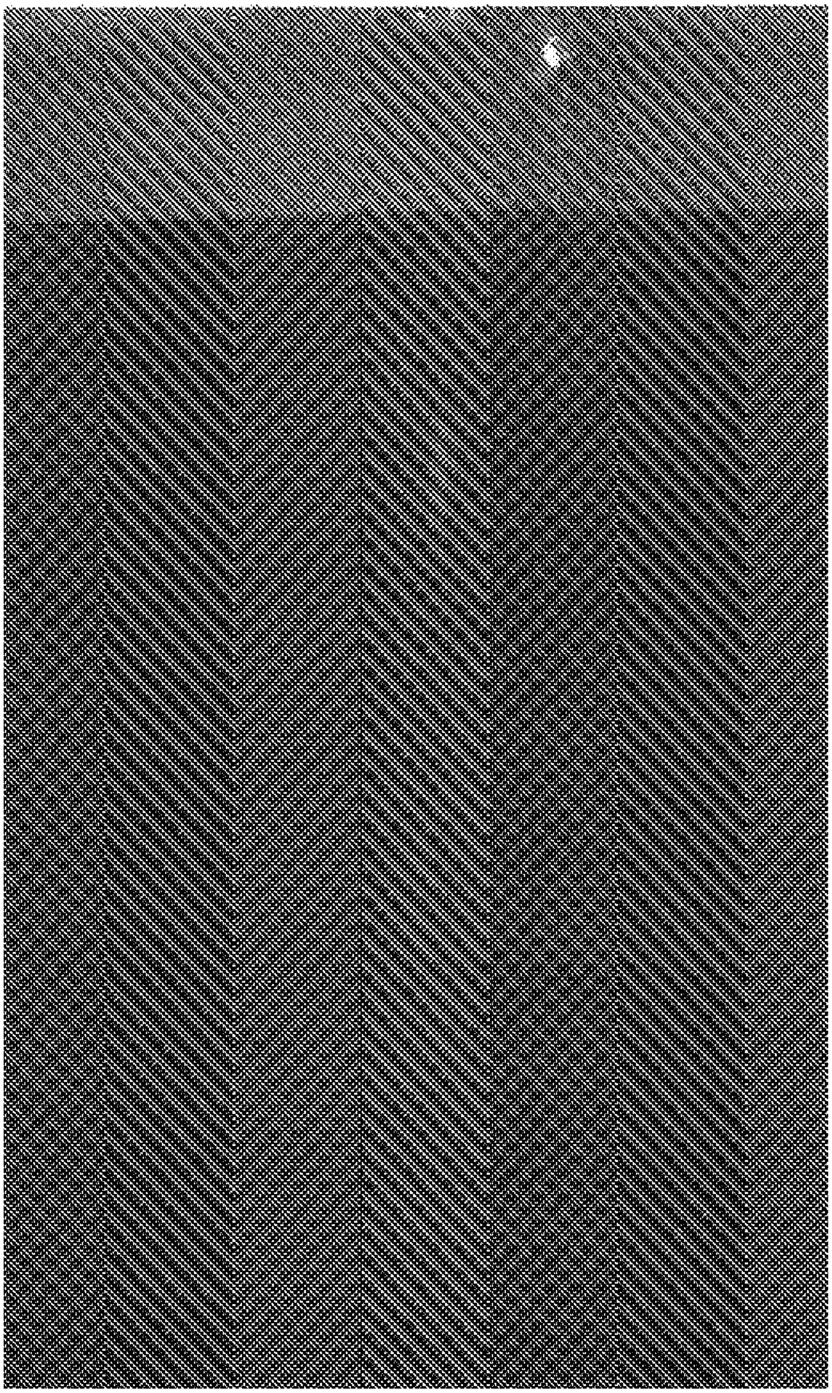
FIG. 18. Color visualization of Water with smartphone spectrum.
Figure 19:
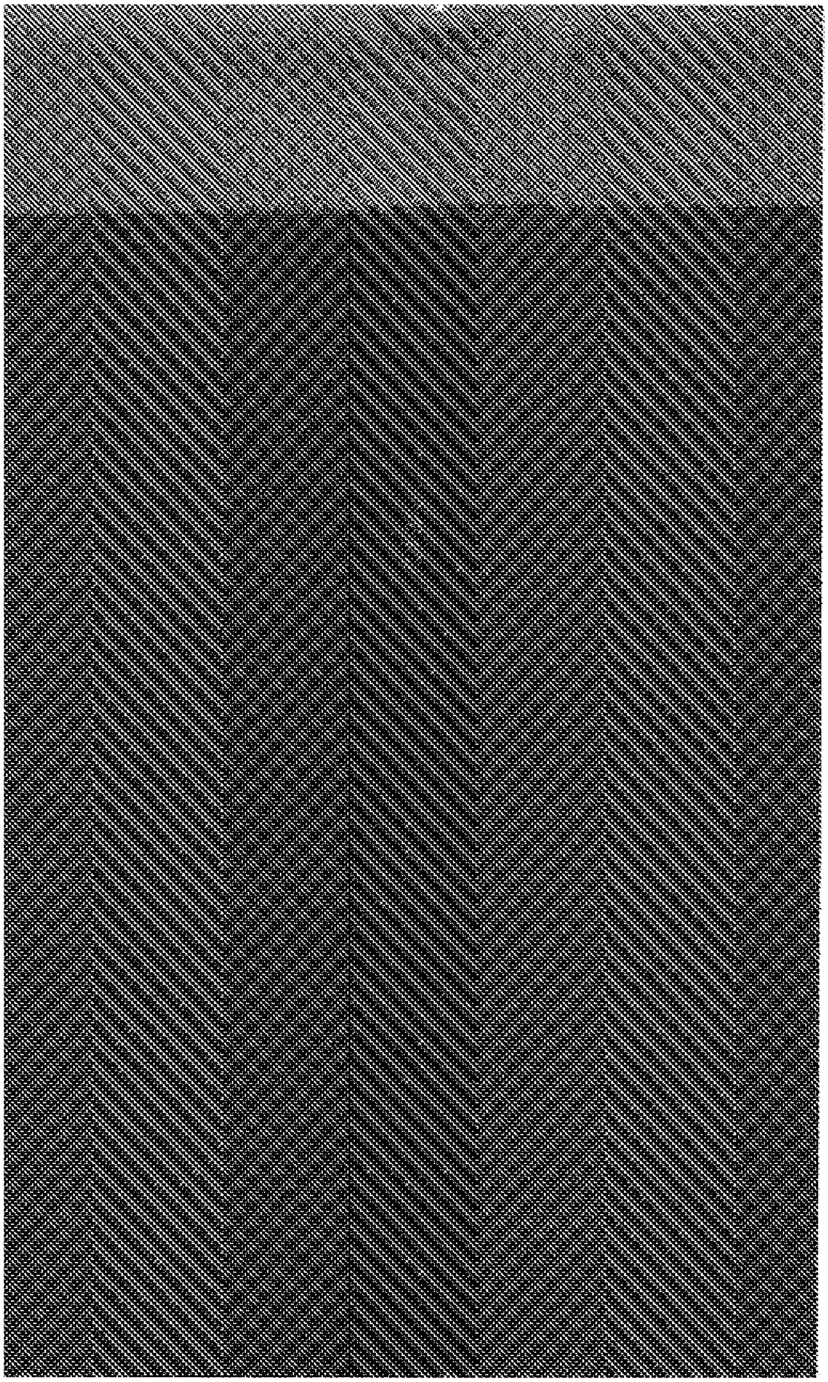
FIG. 19. Tartrazine (0.1 nM) in water visualization with smartphone.

The following data are (FIGS. 14, 17-19) from a optical caustic based spectrometer created using a smart phone, a piece of a CD as a diffraction grating, and the experiment with tartrazine vs, water using a Blue LED. The Blue LED emits from 380-580 nm with a maximum at 430 nm. This is the Blue LED light measured going through a droplet of water using a spectrometer (FIG. 14, 18), A communication device such as a Phone (e.g. Smart Phone) is less expensive and readily available and data can be analyzed centrally while results with a spectrometer will require a more costly apparatus. Furthermore, color visualization rapidly can easily document observe and document results (FIG. 19). This shows that the tartrazine absorbs more light (the grey value only reach 90 or so) and the blue region is nearly all removed. In order to develop a communication device or phone optical caustic fluorimeter, only a small adaptation needs to be made to the apparatus. Prototypes that can adapt several phone bands to capture the data have been developed. A communication device or phone, such as a smart phone and a optical caustic spectrometer are combined to generate a fluorimeter. The fluorimeter is simple and cheaper than those available commercially.

Figure 20:
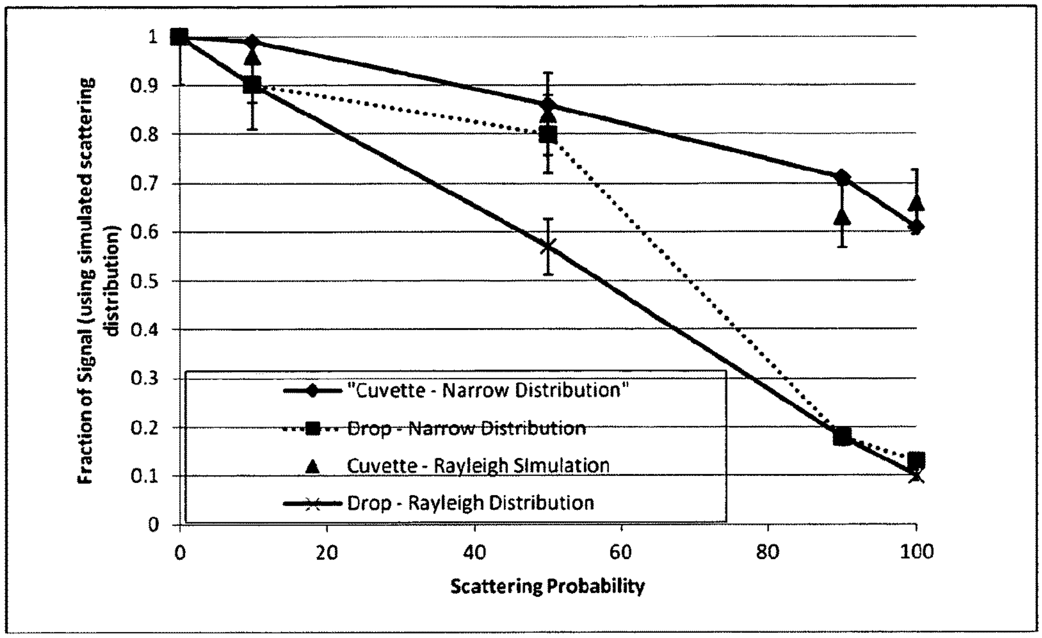
FIG. 20. Simulation Using Ray Tracing with a Monte Carlo Method. Light Scattering angular distribution for the Rayleigh Simulation is given in FIG. 22.
Figure 21:
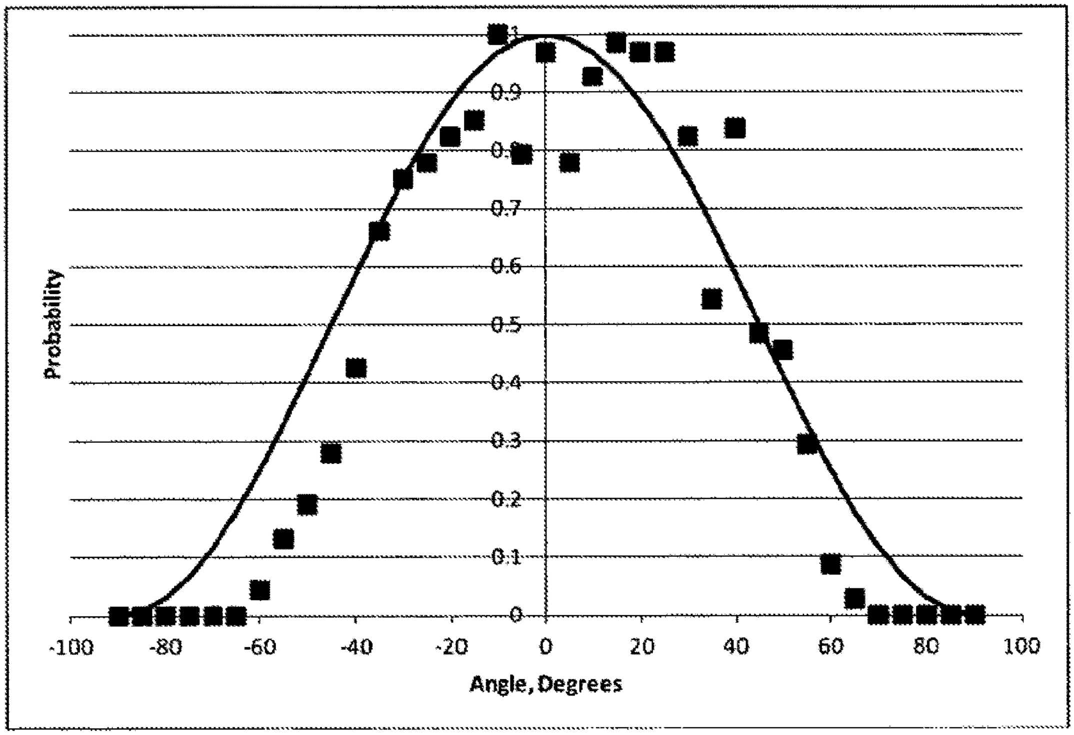
FIG. 21. Representation of Rayleigh Scattering cos 2 (bol) dependence (smooth curve) compared with random number generator used to determine scattering angle in Monte Carlo Method results given in FIG. 20.

Example 11. Optical Response—Scattering Vs. Optical Caustic in a Drop Monte Carlo Simulations A Monte Carlos simulation was used to compare the scattered based data with optical caustic generated data to further demonstrate the advantages of optical caustic from traditional methods. FIG. 20. Simulation Using Ray Tracing with a Monte Carlo Method. Light Scattering angular distribution for the Rayleigh Simulation is given in FIG. 21. Based on these simulations (FIGS. 20-21), optical caustic detection via a droplet is much more sensitive to changes in angular distribution of scattering and the signal is affected by samples with higher scattering. This is observed experimentally when a small amount of different sized gold nanoparticles is added to a suspension and when the refractive index of gold nanoparticles changes slightly due to a reduction in Plasmon Resonance. In both cases, the signal change in the optical caustic detection using a droplet gives more easily measured changes in signal. FIG. 21. Representation of Rayleigh Scattering cos 2(bol) dependence (smooth curve) compared with random number generator used to determine scattering angle in Monte Carlo Method results given in FIG. 20.

Example 12. Comparison Between Optical Caustics and Currently Available Diagnostic Techniques Conventional detection technology of Arboviral infections takes between several days to several weeks, requires costly mobilization of medical crews to the point of infection, and requires blood samples from infected patients, which is often difficult to obtain in a timely fashion in low resource settings or even in developed nations because the results also require continuation by public health officials using their central testing centers. Delays in rapid and cost-effective detection have a devastating economic impact on developing countries. Also, in the U.S., for example, the response can be disproportionate to the number of cases due to public demand for quality care and political pressure. For example, the CDC estimated that $3 million was spent in reaction to rust over 160 human cases of West Nile Virus in Sacramento County in 2005. Another consideration for improved surveillance is that climate change may be contributing to the spread of arboviruses in the United States and to other developed nations.

Traditional analysis of arbovirus has various requirements and features avoided by the optical caustic methods as demonstrated in Table 3.

TABLE 3

Comparison of traditional method vs. optical caustic method.

| Traditional Diagnosis Method | Optical Caustics Method |
|---|---|
| 5 days in laboratory<br>Displacement of instrumental to extract blood<br>Central laboratory is necessary<br>Depends of medical reading (for therefore, subject to error human) | 20 minutes<br>Do not requires displace large equipment<br>Minimum invasive (Requires only drops of blood)<br>It accurate because is quantitative, and can test the environment, mosquitos, or humans<br>Information documented and transmission cellular (form a network of health public) |

Table 3. Comparison of traditional method vs. optical caustic method.

In Table 4, the optical caustic method is compared with specific diagnostic methods used in the field today. Overall, the optical caustic method is faster, cheaper, and easier. The optical caustic apparatus is able to measure environmental, mosquito, or human samples and generate quantitative values in less than 2 minutes.

| | Time, min | Cost per test ($) | Mobility | Utility for Day 1-3 | Ease of Use | Expertise |
|---|---|---|---|---|---|---|
| ELISA | 120-240 | 10-15 | No | No | No | No |
| LFA | 15-20 | 1-3 | No | No | Yes | Yes |
| PAI | 90 | 3 | No | No | Yes | Yes |
| Optical Caustic | 2 | 1 | Yes | Yes | Yes | No |

Table 4. Comparison of Enzyme Linked Immunosorbent Assay (ELISA), Lateral Flow Immunoassay (LFA), and Photo Acoustic Imaging (PAI) with Optical Caustics.

The Optical Caustic method is useful for 1 to 3 day analysis and allows for use in the field due to its mobility.

Example 13 Optical Caustic Online Platform for Surveillance and Monitoring of Arboviruses The optical caustic simplistic apparatus allows for government or community authorities to track and test mosquitos infested areas, this is monitored by a hand held data collector, the information is sent wireless to an authentication/encryption systems which forward the information to a Call Center and safeguards the information to a healthcare storage center. The healthcare storage center can provide physicians with data for analyzes and diagnostics. Individuals can use the hand held data collector, the information is sent wireless to an authentication/encryption systems which forward the information to a Call Center and safeguards the information to a Healthcare Storage Center. The Healthcare Storage Center can provide physicians with data for analyzes and diagnostics. Using the optical caustic apparatus mosquito infested areas can be tracked and information forward to a data storage center and transmitted to health professional for analysis and diagnosis. Furthermore, individuals can use the optical caustic method to collect data and information forward to a data storage center and transmitted to health professional for analysis and diagnosis.

Example 14. Dengue Protein Monitoring Using Optical Caustic Spectrometer

There are an estimated 100 million cases of acute febrile Dengue fever (DF) a year world-wide with about 500,000 leading to severe hemorrhagy and hipovolemic shock (DHF), The Dengue virus is endemic in 112 countries with some outbreaks resulting in over 10,000 cases a day. This is significantly more widespread than 60 years ago when only 9 countries reported Dengue outbreaks, and several of the countries currently reporting had not previously reported Dengue fever or had not reported this disease in 20 years. In 2010, Dengue fever outbreaks occurred in Puerto Rico and in Key West, Fla. The last previously recorded Florida case was in 1934.

Rapid, and accurate Dengue detection poses many challenges due in part to a typical several days lag from the onset of symptoms to a patient's immune system response leading to antibody production. Moreover, it is difficult to distinguish whether a specific infection will leads to DHF, which is a severe disease course that has a high rate of mortality. Experts believe that the current state-of-the art for identifying the most severe form of Dengue fever is by testing for the specific genetic signature of the viral strain(s) that leads to DHF. However, since the cost of equipment and testing at this level of sophistication is beyond the reach of developing and poor nations (where the predominant number of Dengue cases are reported each year) this capability has not seen adoption where it is most needed. Moreover, there is currently no vaccine or specific treatment for the disease, and thus understanding which patients should receive the best care possible is perhaps the most relevant decision-making tool for the health care provider.

The world-wide cost of treating patients is approximately $70 billion which includes the diagnostic costs (about 5% of the cost of care) primarily using clinical assessment based on WHO protocols and; or to a much lesser extent laboratory instrumentation. Diagnosis of Dengue using clinical kits is difficult since antibodies for first time infections take several days to develop and since prior infection requires detection of a different type of antibody, and positivity rates are typically below 40%. In endemic regions a high percentage of the population has anti-Dengue IgG antibodies and test positive due to prior infection making lateral flow immunoassay (LFIA) type tests based on this antibody useless. The current penetration of diagnostic test kits is estimated at less than 10% and probably closer to 5% since only a few major hospitals and centers have clinical laboratories that offer diagnostic tests to confirm the infection.

It is very important to understand how to treat patients as soon as possible since their symptoms vary from a great deal from the absence of symptoms, mild fevers similar to a cold, to for the More severe cases, hemorrhaging. There is no specific treatment of the disease, but instead patient health is supported based on understanding how the disease is progressing, Interestingly, several recent research articles describe monitoring platelet activity, C Reactive Protein, Pentraxin 3 protein, and other biomarkers for Dengue fever patients. These studies indicate that some of these markers may be useful as early indicators of DHF or may serve to help identify other complications due to Dengue fever.

Specific Detection: C Reactive Protein with Human Serum. A commercially available kit for the detection of C Reactive Protein in human serum was used to establish the time dependent signal following a well-established protocol for reading agglutination using a card and visual inspection. The kit contains a high CRP human serum sample (CRP >6 mg/L) and a normal human serum sample (CRP <6 mg/L) for quality assurance testing. Tables 5 and 6 below shows the results of 17 separate experiments with the contents of the kit. In order to conduct the trials, first a drop (20-50 microliters) of the biofluid sample (positive human serum, negative human serum, or distilled water) is placed on the patterned, optical caustic. Next, a similar size droplet of the 100-150 nm latex particle suspension containing anti-CRP antibodies was placed on top of the sample drop. Due to the physics of optical cuastics-water droplet interactions, very rapid mixing occurs and there is no need for the operator to do anything other than collect the data.

Table 5. Results Using Two Laboratory Prototypes with Human Serum Containing High C Reactive Protein

| High | Runs 1 a&b | | Runs 2 a&b | | Runs 3 a&b | | Run #4 | | Run #5 | | Run #6 | |
|---|---|---|---|---|---|---|---|---|---|---|---|---|
| CRP | Slope | $r^2$ | Slope | $r^2$ | Slope | $r^2$ | Slope | $r^2$ | Slope | $r^2$ | Slope | $r^2$ |
| Prototype #1 | −0.24 | 0.96 | −0.16 | 0.96 | −0.16 | 0.98 | −0.15 | 0.90 | −0.19 | 0.95 | −0.13 | 0.96 |
| Prototype #2 | −0.14 | 0.98 | −0.13 | 0.98 | −0.17 | 0.99 | | | | | | |

Average Slope = −0.16 in units of relative light transmitted per minute
Standard Deviation of Slope = ±0.03

Table 6. Results Using Two Laboratory Prototypes with Normal Human Serum

TABLE 6

Results Using Two Laboratory Prototypes with Normal Human Serum

| Normal | Runs 7 a&b | | Runs 8 a&b | | Runs 9 a&b | | Runs 10 a&b | |
|---|---|---|---|---|---|---|---|---|
| CRP | Slope | $r^2$ | Slope | $r^2$ | Slope | $r^2$ | Slope | $r^2$ |
| Prototype #1 | −0.026 | 0.92 | −0.025 | 0.52 | −0.028 | 0.88 | −0.033 | 0.73 |
| Prototype #2 | $-6.8 \times 10^{-5}$ | 0.47 | $1.8 \times 10^{-4}$ | 0.75 | $1.2 \times 10^{-4}$ | 0.84 | $-1.7 \times 10^{-4}$ | 0.84 |

Average Slope = −0.014 in units of relative light transmitted per minute
Standard Deviation of Slope = +/−0.015

Tables 5 and 6. The experimental runs are given for two different kits and two different prototypes. Prototype 1 is the Optical caustics version 1. Prototype 2 uses visible light and a fiber optic spectrometer to collect the data. Human serum samples used to verify test procedures provided by the manufacturer. Mixing is very rapid and the operator only needs to place one drop over the other and wait for a reading. The rate data represent times from 10 90 seconds. As can be seen, the negative human serum samples essentially give a zero reading for the slope, while the High CRP human serum samples gave a clear reading with good agreement between the two instruments even though Prototype #1 uses low cost electronics while Prototype #2 uses visible light and a $4,000 fiber optic spectrometer with a computer.

Figure 22:
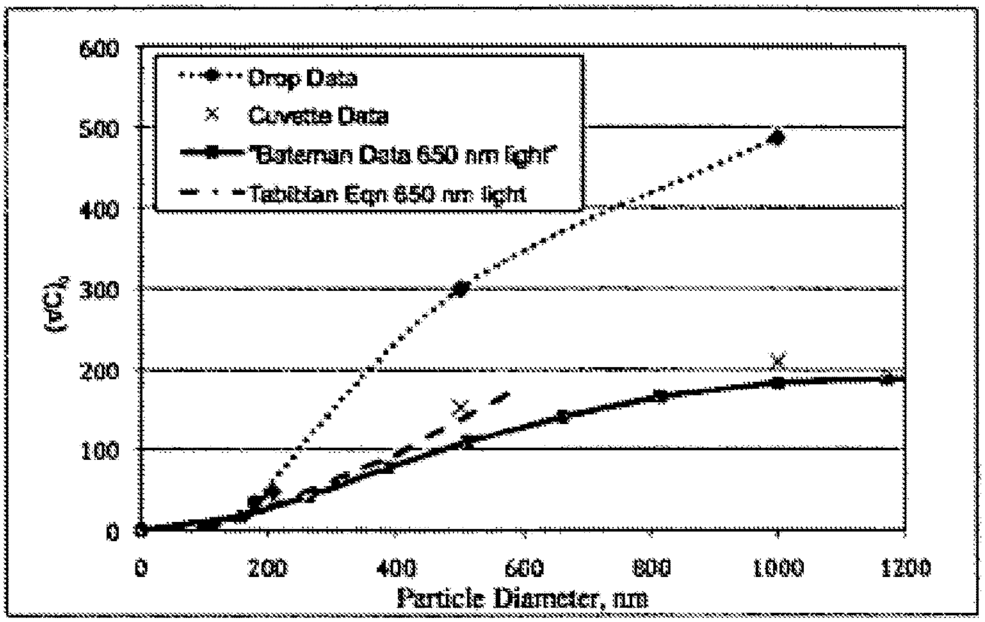
FIG. 22. Comparison of Optical Caustics, Scattering Method, and Theory.
Figure 23:
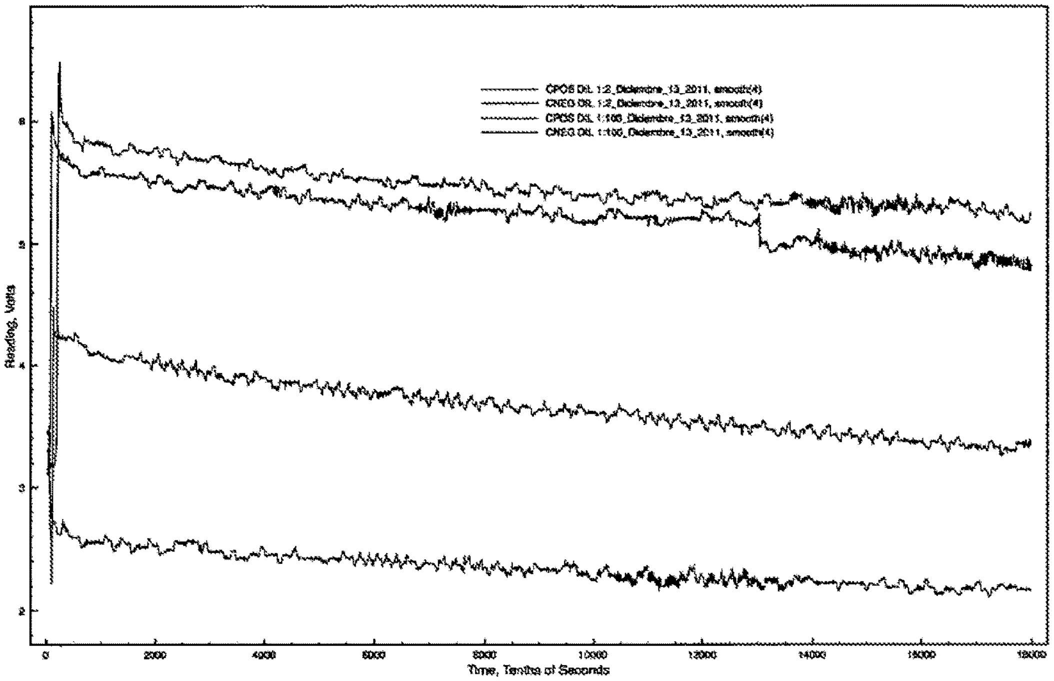
FIG. 23. Optical caustic data with positive and negative NS1 human serum samples (Dengue Type 2) at 1:2 and 1:100 dilutions. The reading in volts is proportional to the intensity of fight measured. The x-axis is in tenths of seconds since the data was collected at 10 Hz.

Non-Specific: Detection: Total Protein. Recently completed experiments measuring total protein due to light scattering when a high concentration of positively charged (amino PSDVB, 220 nm diameter) latex particles is added to biological samples such as human serum, urine, and saliva. The data generate a dynamic reading that undergoes a maximum that correlates with total protein concentration. The optical caustics has been calibrated with BSA droplet solutions over a wide concentration range (1-110 mg/ml) giving a correlation coefficient of r2=0.92. Thus far we have been able to correctly identify that the total Protein in the positive (>6 mg/L CRP) human serum is higher than the negative human serum (<6 mg/L, CRP) and that the diluted serum total protein are at physiologically reasonable values. FIG. 22 below compares cuvette and droplet calibration data using the Optical caustic method and theory using 650 nm light. Agreement among our cuvette data, published data, and the theoretical curve (not shown) is reasonable both in the magnitude of the specific turbidity and the overall shape of the trend with respect to microparticle diameter. However, the optical caustic droplet clearly gives higher specific turbidity at all particle sizes and the trend of the data for particles above 200 nm diameter diverges markedly from the rest of the data and Mie theory. The result of this behavior is that turbidity measurements from a droplet on a optical caustic surface is much more sensitive than a standard turbidity meter, Hence aggregates can be detected when they are present at very low concentrations and relatively small sizes, FIG. 22. Comparison of droplet and cuvette data using the optical caustic method with theory and data.

Other experiments with a fiber optic spectrometer using 2 micrometer diameter particles in a highly concentrated suspension (10 micrograms/ml) of 1 micrometer diameter particles showed a nearly 20% increase in signal when 2 micrometer diameter particles were added at a concentration of 100 nanograms/ml (a 100-fold lower concentration). The same experiment with a cuvette, while yielding a slight increase in signal, was within the margin of error and could not conclusively indicate the presence of the 2 micron particles at this relatively low concentration. It should be noted that the higher specific turbidity and steeper slope for droplets on optical caustic surfaces translate to a dramatic change in readings since turbidity is proportional to the log of the voltage. Thus, the optical caustic method is more sensitive to a change size due to the generation of a high intensity optical caustic and to the additional small angle scattering information from the air/water interface focusing light that undergoes multiple scattering events within the droplet.

The next section summarizes preliminary pilot data collected with human serum for NS1 antigen as an early marker for Dengue Fever. Detection by the droplet, microplate, and a spectrometer are provided as comparisons.

Dengue Antigen Data Collection

This is a summary of the results of our initial experiments with Human Serum samples using 10 nm gold particles with MP Biomedical Monoclonal Dengue NS1 Type 2 antibodies. Experiments where run on one human positive sample (DPOS) and one human negative sample (DNEG) using a microplate reader and the optical caustic based Light Scattering Device. These two samples were diluted in phosphate buffered saline at 1:2 and 1:100. The total numbers of measurements were four, two dilutions each for DPOS and DNEG. The data indicate that both microplate readings at 490 and 630 nm agree with the optical caustic based Light Scattering Device in that the positive sample DPOS showed much smaller absorbance (higher voltage reading on the BioXplor) than the DNEG. The difference is dramatic for both the microplate and BioXplor instruments. Human serum is not known to absorb much light at 490, 630, or 620-640 nm which are the wavelengths used in these experiments, so the difference is believed due to a change in the Plasmon scattering of the gold nanoparticles.

Table 7. A summary of the absorbance data for gold conjugate with anti-NS1 for the Microplate. Based on repeat readings of phosphate buffered saline control wells, reader has an accuracy of 5-10%.

TABLE 7

A summary of the absorbance data for gold conjugate with anti-NS1 for the Microplate. Based on repeat readings of phosphate buffered saline control wells, reader has an accuracy of 5-10%.

| Sample | 490 nm Initial Reading | 490 nm Reading After 230 (for 1:2) or 280 minutes (for 1:100) | 630 nm Initial Reading | 630 nm Reading After 230 (for 1:2) or 280 minutes (for 1:100) |
|---|---|---|---|---|
| DPOS (1:2) | 0.328 | 0.295 | 0.147 | 0.143 |
| DNEG (1:2) | 0.428 | 0.397 | 0.236 | 0.228 |
| Phosphate Buffered Saline (Control) | 0.206 | 0.178 | 0.092 | 0.083 |
| DPOS (1:100) | 0208 | 0.176 | 0.095 | 0.084 |
| DNEG (1:100) | 0.218 | 0.194 | 0.098 | 0.094 |

The table above shows that the positive sample for a 1:2 dilution gives an initial absorbance reading after mixing the gold conjugate with the sample droplet of 23% lower at 490 nm and 38% lower at 630 nm. At a dilution of 1:100, the positive sample droplet is 5% lower at 490 nm and 3% lower initially. The samples decrease in absorbance over time and have similar relative differences. For the optical caustic instrument, the results show the same trend. We have studied the way that the instrument gives data as compared to a spectrometer for gold nanoparticles containing droplets and have found that it gives a more sensitive reading of changes in light scattering than a spectrometer since light that is scattered at angles near 180 degrees (forward scattering) are collected by the instrument. The intensity of light measured initially for the 1:2 ratio samples is 43% higher in the positive samples. Initially, for the 1:100 dilution, the intensity of the positive sample is 7% greater than that of the negative sample droplet.

What is claimed is:

1. A process, for measuring particle size or a particle size distribution of a population of particles, comprising the steps of:

a. providing a light source;

b. providing a first medium;

c. adding particles to the first medium;

d. providing the first medium, with a first curved surface;

e. orienting the light source so that a first ray of light and a second ray of light are targeted at the first medium, wherein:

i. the first ray of light is provided with a first entering vector and a first exiting vector, wherein the first ray of light travels according to the first entering vector upon entering the first medium and then travels according to the first exiting vector upon exiting the first medium; and ii. the second ray of light is provided with a second entering vector and a second exiting vector, wherein the second ray of light travels according to second entering vector upon entering the first medium and then travel according to the second exiting vector upon exiting the first medium f. determining where the first and second exiting vectors form an optical caustic paraxial focus:

g. positioning a detector so that it is located within 30% of the optical caustic paraxial focus;

h. measuring the intensity of the rays of light; and i. determining said particle size or said particle size distribution from the measured intensity.

2. A process according to claim 1, wherein the temperature, pressure, ionic strength surface tension, or molecular composition of the first medium is varied to alter the shape of the first curved surface.

3. The process according to claim 1, wherein particles are 5 nm to 10 μm in size range.

4. A process according to claim 1, wherein:

said first medium comprises a first biological agent selected from the group consisting of proteins, viruses, antibodies, and nucleic acids, said particles comprise moieties which bind to said first biological agent, and wherein said first biological agent is detected by detecting changes in said particle size or said particle size distribution due to aggregation.

5. The process according to claim 4, wherein said first biological agent is detected by detecting changes in said particle size distribution.

6. The process according to claim 4 for use in detecting Dengue virus, wherein:

said first biological agent is C reactive protein; and said moieties are antibodies to C reactive protein.

7. The process according to claim 4, wherein:

said particles are gold nanoparticles conjugated with said moieties;

said moieties are monoclonal Dengue NS1 antibodies; and said first biological agent is Dengue virus.

8. The process according to claim 4, wherein detection of the first biological agent indicates the presence of an infectious disease.

9. The process according to claim 1, wherein the light is any electromagnetic wave.

10. The process according to claim 1, wherein the gravitational force on the first medium is varied to alter the shape of the first curved surface.

11. The process according to claim 1, wherein said particles have a uniform size and composition, and give a unique signal at a given sampling frequency, wherein the signal is attributed to size and composition.

12. The process according to claim 1, wherein the time varying light detected generates information for a specific particle size of interest.

13. The process according to claim 1, wherein the detection of particle size changes can be used to detect target molecules in a sample.

14. The process according to claim 1, wherein the mixtures of particle sizes cause a mixed signal that can be interpreted to determine the change in the overall particle population size.

15. A system for detecting changes in particle size or particle size distribution of a population of particles, comprising:

a. a medium that includes a particle, wherein the medium is a liquid phase and the particle is suspended within the medium to form a particle-suspension; and b. an apparatus comprising i. a non-monochromatic light source that emits a plurality of a non-monochromatic rays;

ii. a detector positioned opposite the light source; and iii. a means for holding a droplet of the particle-suspension between said light source and said detector, wherein the droplet is provided with a curved surface;

wherein the droplet focuses light from said light source at an optical caustic paraxial focus; and wherein the detector detects light intensity at said optical caustic paraxial focus.

16. The system of claim 15, wherein the means for holding a droplet is a spherical container.

17. The system of claim 15, wherein the means for holding a droplet is a surface which allows water to bead into a sphere.

18. A process, for measuring changes in particle size or a particle size distribution of a population of particles, comprising the steps of:

a. providing a light source;

b. providing a first medium;

c. adding particles to the first medium;

d. providing the first medium, with a first curved surface;

e. orienting the light source so that light is refracted by the first curved surface of the first medium so as to form an optical caustic interference pattern;

f. positioning a detector so that it is located 180° from the light source at a paraxial focus of the optical caustic interference pattern;

g. measuring the intensity of the rays of light at the optical caustic interference pattern; and h. detecting changes in said particle size or said particle size distribution from changes in the measured intensity or changes in the optical caustic interference pattern.

19. The system according to claim 15, wherein:

said droplet has a defined shape having a curved surface;

said defined shape being spherical, spheroidal, toroidal, hemispherical, hyperboloidal, conical, or ellipsoidal.

20. The process of claim 4, said method further comprising sending the detected changes in particle size or particle size distribution wirelessly to health professionals for analysis and diagnosis as a surveillance and monitoring tool.

21. The process according to claim 8, wherein detection of the first biological agent indicates the presence of an infectious disease selected from the group consisting of acinetobacter infection, actinomycosis, African trypanosomiasis, AIDS, Amebiasis, Anaplasmosis, Anthrax, Arcanobacterium baemolyticum, Argentine hemorrhagic fever, Ascariasis, Aspergillosis, Astrovirus infection, babesiosis, bacillus cereus infection, bacterial pneumonia, bacterial vaginosis, bacteroides infection, Balantidiasis, Bavlisacaris infection, BK virus infection, Black piedra, Bolivian hemorrhagic fever, Botulim, Brazilian hemorrhagic fever, Brucellosis, Burkhoideria infection, Buruli ulcer, calicivirus, Norovirus, Sapoviras, campylobacteriosis, Candidiasis, cat-scatch disease, cellulitis, Chagas disease, chancroid, chickenpox, chlamydia, cholera, chromoblastomysis, clonorchiasis, Clostridium difficile, coccidioidomycosis, Colorado tick fever, common cold, Creutzfeidt-jakob disease, Crimean-Congo hemorrhagic fever, Cryptococcosis, Crytosporidiosis, Cytomegalovirus, Dengue fever, Diphtheria, Ebola hemorrhagic fever, Echinococcosis, Epidemic typhus, Faciolosis, Glaners, Hantavirus, Hepatisis A-E, Herpes, Hookworm, human metapneumovirus, HPV, influenza, keratosis, kiiru, lassa fever, leishmaniasis, lyme disease, Malaria, Marburg hemorrhagic fever, mumps, Murine typhus, mycoplasma pneumonia, mycetoma, Myiasis, Norcadiosis, Onchocerciasis, Para gonimiasis, Pasteurellosis, Pediculosis corporis, Pediculosis pubis, Pertussis, Plague, Pneumocystid pneumonia, Q fever, Rabies, RSV, Rhinovirus infection, Rift Valley fever, rotavirus, Rubella, Salmonellosis, Scabies, Shingles, Syphilis, Tetanus, Tinea capitis, trichomoniasis, Tuberculosis, Venezuelan equine encephalitis, Venezuelan hemorrhagic fever, West Niles fever, White Piedra, Yellow fever, and Zygomycosis.

* * * * *